United States Patent
Batchelor et al.

(10) Patent No.: US 12,371,404 B2
(45) Date of Patent: *Jul. 29, 2025

(54) FUSED BICYCLIC ALKYLENE LINKED IMIDODICARBONIMIDIC DIAMIDES, METHODS FOR SYNTHESIS, AND USES IN THERAPY

(71) Applicant: NovaTarg, Inc., Research Triangle Park, NC (US)

(72) Inventors: Kenneth Batchelor, Wilmington, NC (US); Jeffery E. Cobb, Chapel Hill, NC (US); Kristjan S. Gudmundsson, Raleigh, NC (US); Brad R. Henke, Cary, NC (US); Francis X. Tavares, Durham, NC (US)

(73) Assignee: NovaTarg, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/384,197

(22) Filed: Oct. 26, 2023

(65) Prior Publication Data

US 2024/0327350 A1    Oct. 3, 2024

Related U.S. Application Data

(60) Continuation of application No. 17/578,050, filed on Jan. 18, 2022, now Pat. No. 11,834,411, which is a division of application No. 16/467,136, filed as application No. PCT/US2017/065095 on Dec. 7, 2017, now Pat. No. 11,261,157.

(60) Provisional application No. 62/454,147, filed on Feb. 3, 2017, provisional application No. 62/431,475, filed on Dec. 8, 2016.

(51) Int. Cl.
*C07D 209/20* (2006.01)
*A61P 3/10* (2006.01)
*C07D 209/32* (2006.01)
*C07D 471/04* (2006.01)

(52) U.S. Cl.
CPC ........... *C07D 209/20* (2013.01); *A61P 3/10* (2018.01); *C07D 209/32* (2013.01); *C07D 471/04* (2013.01)

(58) Field of Classification Search
CPC .................................................. C07D 209/20
See application file for complete search history.

(56) References Cited

U.S. PATENT DOCUMENTS

| | | |
|---|---|---|
| 3,152,181 A | 10/1964 | Shapiro et al. |
| 5,322,858 A | 6/1994 | Canfield et al. |
| 6,169,107 B1 | 1/2001 | Kitano et al. |
| 8,796,338 B2 | 8/2014 | Baron et al. |
| 11,261,157 B2 * | 3/2022 | Batchelor ............... A61K 45/06 |
| 11,834,411 B2 * | 12/2023 | Batchelor ................ A61P 3/10 |
| 2012/0283299 A1 | 11/2012 | Kim et al. |

FOREIGN PATENT DOCUMENTS

WO    2015/160220 A1    10/2015

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*
"Find ETDs Home » Thesis Resources » Find ETDs" Online: "https://ndltd.org/thesis-resources/find-etds/" Accessed Jan. 31, 2023.*
Irwin "Zinc—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/Zregistry (CAS Registrysm) Sep. 2016 2 pages.*
Pubchem CID: 3373692, Create Date Jul. 7, 2005, pp. 1-14.
International Search Report, International Application No. PCT/US17/65095 filed Dec. 7, 2017, mailed Feb. 22, 2018.
West (West, Solid State Chemistry and Its Applications, John Wiley & Sons, 1984).
Pletnev, Khimiko-Famatsevticheskii Zhurnal (1972), 6(3), 27-9.
Hardie, "AMPK: Positive and Negative Regulation, and its Role in Whole-Body Energy Homeostasis", Current Opinion in Cell Biology, 2015, 33:1-7.
Hardie et al., "AMPK: An Energy-Sensing Pathway with Multiple Inputs and Outputs", Trends in Cell Biology, Mar. 2016, vol. 26, No. 3, 190-201.
Rabinovitch et al., "AMPK Maintains Celllular Metabolic Homeostasis through Regulation of Mitochondrial Reactive Oxygen Species", Cell Reports 21, 1-9, Oct. 3, 2017.

* cited by examiner

*Primary Examiner* — Nizal S Chandrakumar
(74) *Attorney, Agent, or Firm* — Barnes & Thornburg LLP

(57) ABSTRACT

The present invention provides novel fused bicyclic alkylene linked imidodicarbonimidic diamides. In particular, described herein are N-[2-(indol-3-yl)alkylene]-linked imidodicarbonimidic diamides and N-[2-(pyrrolopyridin-3-yl) alkylene]-linked imidodicarbonimidic diamides (compound of formula (I) or formula (II)), and uses therefor. The compounds of the present invention are believed to be organic cation transporter selective compounds, useful for the treatment of diseases and conditions caused by reduced activity of 5' adenosine monophosphate-activated protein kinase (AMPK).

1 Claim, 2 Drawing Sheets

FUSED BICYCLIC ALKYLENE LINKED IMIDODICARBONIMIDIC DIAMIDES, METHODS FOR SYNTHESIS, AND USES IN THERAPY

CROSS-REFERENCE TO RELATED APPLICATIONS

This application is a continuation of U.S. application Ser. No. 17/578,050, filed Jan. 18, 2022, which is a divisional of U.S. application Ser. No. 16/467,136, filed Jun. 6, 2019, which is a § 371 of international application PCT/US2017/065095, filed Dec. 7, 2017, which claims the benefit of U.S. Provisional Patent Application No. 62/431,475, filed Dec. 8, 2016, and U.S. Provisional Patent Application No. 62/454,147, filed Feb. 3, 2017, the entire contents of each of which are hereby incorporated by reference.

FEDERALLY SPONSORED RESEARCH

This invention was made with government support under the following: Novel and Selective AMPK Activator for the Treatment of Hepatocellular Carcinoma, 1R43CA171389-01A1, Novel Biguanides to Treat Type 2 Diabetes, 2R44DK096803-02, and Novel and Kidney Selective AMPK Activators to Treat Polycystic Kidney Disease, 2R44DK098959-02, awarded by National Institutes of Health. The government has certain rights in the invention.

FIELD OF THE INVENTION

The present invention provides novel fused bicyclic alkylene linked imidodicarbonimidic diamides. In particular, described herein are N-[2-(indol-3-yl)alkylene]-linked imidodicarbonimidic diamides and N-[2-(pyrrolopyridin-3-yl)alkylene]-linked imidodicarbonimidic diamides (compound of formula (I) or formula (II), and uses therefor. The compounds of the present invention are believed to be organic cation transporter selective compounds, useful for the treatment of diseases and conditions caused by reduced activity of 5' adenosine monophosphate-activated protein kinase (AMPK).

BACKGROUND OF THE INVENTION

In medieval times, the French lilac (*Galega officinalis*) was used in Southern and Eastern Europe to treat diabetes. Guanidine, the active ingredient in French lilac, was found to possess hypoglycemic activity in 1918, but its clinical use was limited by its toxicity. Biguanides were developed from guanidine and investigated for the treatment of diabetes. The biguanide, metformin, was described in the literature in 1922 and was shown to reduce blood sugar in rabbits. Metformin was approved for treatment of type 2 diabetes (T2D) in the UK in 1958. Several analogs of metformin were studied in the 1950s and a more potent analog, phenformin, was approved in the US in 1959 (marketed as DBI by Ciba-Geigy). See, Shapiro S. L., Parrino V. A., Freedman L. *Hypoglycemic Agents. III. N-alkyl- and aralkylbiguanides.* J Am Chem Soc. 1959; 81:3728-3736 and Shapiro S. L., and L. Freedman, *Oral Anti-Diabetic Compositions and Methods*, U.S. Pat. No. 2,961,377, Nov. 22, 1960, each incorporated by reference herein with regard to the background of buguanides.

At the time that metformin and phenformin were being studied, it was not known how these molecules entered cells. Both metformin and phenformin are protonated and highly cationic at physiological pH. Recently it has been shown that biguanides, such as metformin and phenformin, are transported into liver cells by organic cationic transporter 1 (OCT1), whereas a different organic cation transporter, OCT2 in the kidney, plays an important role in renal elimination. See, e.g., Choi M. K., Song I. S. Organic cation transporters and their pharmacokinetic and pharmacodynamic consequences. Drug Metab Pharmacokinet. 2008, 23(4): 243-53 and Koepsell H, Lips K, Volk C. *Polyspecific Organic Cation Transporters: Structure, Function, Physiological Roles, and Biopharmaceutical Implications*. Pharmaceutical Research. 2007; 24:1227-1258, each incorporated by reference for background teaching. OCT1 plays a key role in hepatic uptake of metformin and its therapeutic efficacy. In OCT1-deficient mice (OCT1–/– genotype) the glucose lowering effect of metformin is completely abolished. See, Shu, Y., S. A. Sheardown, C. Brown, R. P. Owen, S. Zhang, R. A. Castro, et al., *Effect of genetic variation in the organic cation transporter 1 (OCT1) on metformin action*. J Clin Invest, 2007. 117(5): 1422-31, herein incorporated by reference for background teaching. OCT1 is highly polymorphic in humans and OCT1 polymorphism has been shown to affect the response of healthy human volunteers to metformin, demonstrating the importance of OCT1 for therapeutic efficacy. See, Chen, L., M. Takizawa, E. Chen, A. Schlessinger, J. Segenthelar, J. H. Choi, A. Sali, M. Kubo, S. Nakamura, Y. Iwamoto, N. Iwasaki, and K. M. Giacomini, *Genetic polymorphisms in organic cation transporter 1 (OCT1) in Chinese and Japanese populations exhibit altered function*, J Pharm Exper Therap 2010. 335: 42-50 and Shikata, E., R. Yamamoto, H. Takane, C. Shigemasa, T. Ikeda, K. Otsubo, et al., *Human organic cation transporter (OCT1 and OCT2) gene polymorphisms and therapeutic effects of metformin*. J Hum Genet, 2007. 52 (2): 117-22, each incorporated herein by reference with regard to background teaching.

Metformin and phenformin are both transported by OCT1, OCT2, OCT3, and MATE1 (Multidrug And Toxin Extrusion). While phenformin is a better substrate than metformin for the organic cation transporters, neither metformin nor phenformin show selectivity for any particular transporter. Since metformin can stimulate lactate accumulation in the liver, one side effect of this class of compounds can be lactic acidosis. Organic cation transporters (OCTs) are endogenous proteins, including OCT1, OCT2, OCT3, PMAT (plasma membrane monoamine transporter), and MATE1, which serve as transporters of various cations into and out of cells. Such cations may themselves be endogenous or may be synthetic medicaments such as the cationic form of the drug cimetidine. Cimetidine has high affinity for OCT2 and can block renal elimination of metformin. See, Somogyi, A., Stockley, C., Keal, J., Rolan, P. and F. Bochner. *Reduction of Metformin Renal Tubular Secretion by Cimetidine in Man*. Brit J Clin Pharmacol 23:545-551 (1987), herein incorporated by reference with regard to background teaching. If 2 or more medicaments are administered to a patient, the OCT transport profile of the medicaments when administered alone may be altered significantly. Such may be characterized as a drug-drug interaction of concern to health care professionals. It is thus desirable to determine how novel drugs are transported by OCTs and, in particular, which OCT since the drug half-life, drug-drug interaction, peak concentration and area under the curve (AUC) of blood levels may all be affected.

Biguanide derivatives which have been investigated for their antidiabetic or anticancer activities include metformin, phenformin, and buformin. None of these previously studied biguanides, however, have selectivity for any of these transporters. Importantly, an association between activity at these transporters and functional activity of biguanides has not been reported.

Biguanides activate AMPK which is a key regulator of cellular energy utilization. See, Beck, E. and A. J. Scheen, *Anti-cancer activity of metformin: new perspectives for an old drug*. Rev Med Suisse, 2010. 6 (260): 1601-7, herein incorporated by reference with regard to background teaching. Activation of AMPK shifts the cell to an energy producing state: increasing fatty acid uptake and oxidation, glucose uptake and glycolysis, and mitochondrial biogenesis; decreasing fatty acid, cholesterol and protein biosynthesis, gluconeogensis and glycogen synthesis. See, Long, Y. C. and J. R. Zierath, *AMP-activated protein kinase signaling in metabolic regulation*. J Clin Invest, 2006. 116 (7): 1776-83, herein incorporated by reference with regard to background teaching.

There is considerable evidence that metformin can reduce cancer risk in diabetic patients. Several retrospective studies have shown that T2D patients have an increased cancer mortality compared with non-diabetics, but that patients treated with metformin have a substantially (~40%) reduced cancer burden than patients on other treatments. See, Giovannucci, E., D. M. Harlan, M. C. Archer, R. M. Bergenstal, S. M. Gapstur, L. A. Habel, et al. *Diabetes and cancer: a consensus report*. CA Cancer J Clin, 2010. 60 (4): 207-21 and Johnson, J. A. and M. Pollak, *Insulin, glucose and the increased risk of cancer in patients with type 2 diabetes*. Diabetologia, 2010. 53 (10): 2086-8, each incorporated herein with regard to background teaching. Recently, a study of patients who received neoadjuvant chemotherapy for breast cancer showed that diabetic cancer patients taking metformin during their chemotherapy had a higher pathological complete response rate than diabetic patients not receiving metformin (24% versus 8%, P=0.007). See, Jiralerspong, S., S. L. Palla, S. H. Giordano, F. Meric-Bernstam, C. Liedtke, C. M. Barnett, et al., *Metformin and pathologic complete responses to neoadjuvant chemotherapy in diabetic patients with breast cancer*. J Clin Oncol, 2009. 27 (20): 3297-302, herein incorporated by reference with regard to background teaching. Further support for the investigation of metformin for breast cancer prevention is provided by a study showing a 56% decrease in breast cancer among diabetic patients receiving metformin compared with those on other therapies. See, Bodmer, M., C. Meier, S. Krahenbuhl, S. S. Jick, and C. R. Meier, *Long-term metformin use is associated with decreased risk of breast cancer*. Diabetes Care, 2010. 33 (6): 1304-8, herein incorporated by reference with regard to background teaching. These and other results have spearheaded several clinical trials evaluating the use of metformin for breast cancer. Reviewed in Jalving, M., J. A. Gietema, J. D. Lefrandt, S. de Jong, A. K. Reyners, R. O. Gans, et al., *Metformin: taking away the candy for cancer?* Eur J Cancer, 2010. 46 (13): 2369-80, herein incorporated by reference with regard to such teaching. Similar studies have shown that metformin is also effective against other cancers, including colorectal cancer. See, Hosono, K., H. Endo, H. Takahashi, M. Sugiyama, E. Sakai, T. Uchiyama, et al., *Metformin suppresses colorectal aberrant crypt foci in a short-term clinical trial*. Cancer Prev Res (Phila), 2010, 3 (9): 1077-83, herein incorporated by reference.

Metformin is a first line drug for T2D and, as such, is the most prescribed medicine in the world to manage diabetes. See, Kirpichnikov, D., S. I. McFarlane, and J. R. Sowers, *Metformin: an update, Ann Intern Med*, 2002. 137:25-33 and Bailey, C. F, and C. Day, *Metformin: its botanical background*. Pract Diab Int, 2004. 21:115-117, herein incorporated by reference with regard to background teaching. Metformin's advantages over other drugs include a reduction in hepatic glucose output, weight loss, and an increase in insulin sensitivity. See, Hermann, L. S. *Metformin: a review of history, pharmacodynamics and therapy*, Diabetes Metab Rev, 1979. 5:233-245 and Campbell, I. W., and H. C. S. Howlett, *Worldwide experience of metformin as an effective glucose-lowering agent: a meta-analysis*. Diabetes Metab Rev, 1995. 11: S57-S62, herein incorporated by reference with regard to background teaching. Notwithstanding the widespread use of metformin in the treatment of T2D, many patients do not benefit from this drug because of its poor gastrointestinal (GI) tolerability and safety risk. Metformin is contraindicated for use in patients with impaired renal function and the U.S. label carries a blackbox warning because of the risk of life threatening lactic acidosis. There is a need, therefore, for a liver-selective biguanide, which may avoid elimination in the kidney, have improved pharmacokinetic properties, and have a lower risk of causing lactic acidosis.

Non-alcoholic steatohepatitis (NASH) is a progressive fatty liver disease associated with insulin resistance. When metformin was used to treat NASH (dose up to 1 g twice daily (BID)), metformin led to improvement in liver pathology and ALT in 30% of patients. See, Loomba R., Lutchman G., Kleiner D. E., Ricks M., Feld J. J., Borg B. B, Modi A., Nagabhyru P., Sumner A. E., Liang T. J. and J. H. Hoofnagle. *Clinical trial: pilot study of metformin for the treatment of non-alcoholic steatohepatitis*. Aliment Pharmacol Ther. 2009; 29 (2): 172-182, herein incorporated by reference with regard to background teaching. Liver-specific biguanides would be expected to be more efficacious and have a lower risk of causing lactic acidosis.

It has been reported that infection of the liver by hepatitis C virus inhibits AMPK activity and that activators of AMPK can inhibit replication of the hepatitis C virus (Jamel Mankouri, Philip R. Tedbury, Sarah Gretton, Mair E. Hughes, Stephen D. C. Griffin, Mark. L. Dallas, Kevin A. Green, D. Grahame Hardie, Chris Peers, and Mark Harris. *Enhanced hepatitis C virus genome replication and lipid accumulation mediated by inhibition of AMP-activated protein kinase*. PNAS. 2010; 107 (25): 11549-11554, herein incorporated by reference with regard to background teaching). Among the AMPK activators used in this study was the biguanide metformin.

The ability of metformin to prevent cancer has been discussed, however, it is now being considered as a drug to treat certain cancers. See, Jacek Kasznicki, Agnieszka Sliwinska and Józef Drzewoski. *Metformin in cancer prevention and therapy*. Ann Transl Med 2014; 2 (6): 57-67, herein incorporated by reference with regard to background teaching. Thus, cancers which express organic cation transporters are potential targets for metformin and other drugs of the biguanide class. In particular, biguanides with improved potency and safety compared with metformin are expected to be more efficacious for the treatment of cancers that express organic cation transporters, eg endometrial cancer, hepatocellular carcinoma, ovarian cancer, breast cancer, pancreatic cancer, colorectal cancer, lung cancer, prostate cancer, desmoplastic small round cell tumors, and renal cell carcinoma.

Cystic diseases, such as polycystic ovary syndrome, have been shown to respond to treatment with metformin (see, Hany Lashen. Role of metformin in the management of polycystic ovary syndrome. Ther Adv Endocrinol Metab.

2010 June; 1(3): 117-128, herein incorporated by reference with regard to background teaching). Further, experimental studies have suggested the potential for biguanide AMPK activators to treat polycystic kidney disease. See, Vinita Takiar, Saori Nishio, Patricia Seo-Mayer, J. Darwin King, Jr., Hui Li, Li Zhang, Anil Karihaloo, Kenneth R. Hallows, Stefan Somlo, and Michael J. Caplan. *Activating AMP-activated protein kinase(AMPK) slows renal cystogenesis.* PNAS 20011, 108:2462-2467, herein incorporated by reference with regard to background teaching.

Studies have demonstrated the potential of metformin to treat diseases of aging and aging itself. See, Barzilai N, Crandall J P, Kritchevsky S B, Espeland M A. *Metformin as a Tool to Target Aging. Cell Metab.* 2016; 23(6): 1060-5 and Martin-Montalvo A, Mercken E M, Mitchell S J, Palacios H H, Mote P L, Scheibye-Knudsen M, et al. *Metformin improves healthspan and lifespan in mice.* Nature communications. 2013; 4:2192, both herein incorporated by reference with regard to background teaching.

Additionally, there is a link between type 2 diabetes and Alzheimer's disease. See, Li N, Song D S, Leng X. *Link between type 2 diabetes and Alzheimer's disease: from epidemiology to mechanism and treatment.* Clinical Interventions in Aging. 2015; 10:549-560, herein incorporated by reference with regard to background teaching. These studies, though promising, suggest that a more potent and safe biguanide would be even more efficacious. As research progresses on the effect of biguanides on the aging process, the inventors hypothesize that such compounds may have a positive effect on the development of dementia and Alzheimer's disease.

BRIEF SUMMARY OF THE INVENTION

The present invention includes a compound of the formula (I), including salts and solvates thereof. The compounds of formula (I) are believed to be potent ligands for organic cation transporters (OCT1, OCT2, OCT3, PMAT, and/or MATE1). The present invention includes use of the compounds of formula (I) for the treatment of metabolic diseases, especially those caused by reduced activity of AMPK.

One embodiment of the present invention includes a compound of Formula (I):

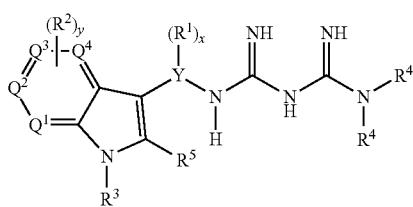

(I)

wherein:
each of $Q^1$, $Q^2$, $Q^3$, and $Q^4$ independently is CH or N, provided not more than two of $Q^1$, $Q^2$, $Q^3$, and $Q^4$ is N and provided two N atoms are not adjacent;
Y is $C_1$-$C_4$ alkylene;
each $R^1$ independently is
i) $C_1$-$C_4$ alkyl,
ii) $C_1$-$C_4$ haloalkyl,
iii) $OR^5$,
iv) $SR^5$,
v) $S(O)R^5$,
vi) $S(O)_2R^5$, or
vii) $N(R^5)_2$,
wherein each $R^5$ independently is hydrogen, $C_1$-$C_4$ alkyl, or $C_1$-$C_4$ haloalkyl;
x is 0, 1, 2, 3, 4, 5, 6, 7, or 8;
$R^2$ is:
i) halogen,
ii) $(CH_2)_mOH$, wherein m is 0, 1, 2, 3, or 4,
iii) $C_1$-$C_4$ alkyl,
iv) $C_1$-$C_4$ haloalkyl,
v) $C_2$-$C_6$ alkenyl,
vi) $C_2$-$C_6$ haloalkenyl,
vii) $C_2$-$C_6$ alkynyl,
viii) $C_2$-$C_6$ haloalkynyl,
ix) $NO_2$,
x) $OR^6$,
xi) $C(O)_2R^6$,
xii) $SR^6$,
xiii) $S(O)R^6$,
xiv) $S(O)_2R^6$, or
xv) $N(R^6)_2$,
wherein each $R^6$ independently is hydrogen, $C_{1-4}$ alkyl, $C_{1-4}$ haloalkyl, or hydroxy-$C_{1-4}$ alkyl;
y is 0, 1, 2, 3, 4, or 5;
$R^3$ is
i) hydrogen,
ii) $(CH_2)_nOH$, wherein n is 0, 1, 2, 3, or 4,
iii) $C_1$-$C_4$ alkyl,
iv) $C_1$-$C_4$ haloalkyl,
v) $C_2$-$C_6$ alkenyl,
vi) $C_2$-$C_6$ haloalkenyl,
vii) $C_2$-$C_6$ alkynyl,
viii) $C_2$-$C_6$ haloalkynyl,
ix) $C(O)_2R^7$,
x) $SR^7$,
xi) $S(O)R^7$,
xii) $S(O)_2R^7$, or
wherein each $R^7$ independently is hydrogen, $C_{1-4}$ alkyl, $C_{1-4}$ haloalkyl, or hydroxy-$C_{1-4}$ alkyl;
each $R^4$ independently is hydrogen, $C_1$-$C_4$ alkyl, or $C_1$-$C_4$ haloalkyl; and
$R^5$ independently is:
i) Hydrogen,
ii) halogen,
iii) $(CH_2)_mOH$, wherein m is 0, 1, 2, 3, or 4,
iv) $C_1$-$C_4$ alkyl,
v) $C_1$-$C_4$ haloalkyl,
vi) $C_2$-$C_6$ alkenyl,
vii) $C_2$-$C_6$ haloalkenyl,
viii) $C_2$-$C_6$ alkynyl,
ix) $C_2$-$C_6$ haloalkynyl,
x) $NO_2$,
xi) $OR^8$,
xii) $C(O)_2R^8$,
xiii) $SR^8$,
xiv) $S(O)R^8$,
xv) $S(O)_2R^8$, or
xvi) $N(R^8)_2$,
wherein each $R^8$ independently is hydrogen, $C_{1-4}$ alkyl, $C_{1-4}$ haloalkyl, or hydroxy-$C_{1-4}$ alkyl;
further wherein:
when Y is ethylene and x is 0, then y is not 0;
when Y is ethylene and x is 0 and y is 1, then $R^2$ is not 5-methoxy;
when Y is ethylene, x is 1, and $R^1$ is 2-methyl, then y is not 0;
or a pharmaceutically acceptable salt or solvate thereof.

Another embodiment of the present invention includes a compound of Formula (II):

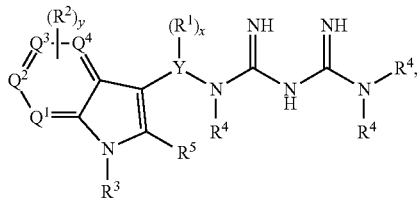

wherein $R^1$, $R^2$, $R^3$, $R^4$, $R^5$, $Q^1$, $Q^2$, $Q^3$, $Q^4$, x, and y are as defined above.

One aspect of the present invention is wherein Y is $C_{1-3}$ alkylene.

One aspect of the present invention is wherein Y is ethylene.

One aspect of the present invention is wherein x is 0, 1, or 2.

One aspect of the present invention is wherein $R^1$ is $C_{1-4}$ alkyl.

One aspect of the present invention is wherein $R^3$ is hydrogen.

One aspect of the present invention is wherein $R^3$ is $C_{1-4}$ alkyl or $(CH_2)_nOH$.

One aspect of the present invention is wherein y is 0.

One aspect of the present invention is wherein y is 1; and $R^2$ is halogen, $C_{1-4}$ alkyl, $OR_6$, or $NO_2$.

One aspect of the present invention is wherein each $R^4$ is hydrogen.

One embodiment of the present invention includes a method for the treatment of a disease in a mammal caused by reduced activity of AMPK which comprises administration of an effective amount of a compound of the present invention.

One aspect of the present invention is wherein the disease is cancer, including but not limited to endometrial cancer, hepatocellular carcinoma, ovarian cancer, breast cancer, pancreatic cancer, colorectal cancer, lung cancer, prostate cancer, desmoplastic small round cell tumors, and renal cell carcinoma.

One aspect of the present invention is wherein the disease is one or more metabolic disorders, including but not limited to Type 2 Diabetes, pre-diabetes, hyperglycemia, Cushing disease, gestational diabetes, phenylketonuria, metabolic syndrome, syndrome X, and Tay-Sachs disease. In one embodiment, the disease is Type 2 Diabetes.

One aspect of the present invention is wherein the disease is liver disease, including but not limited to fatty liver disease.

One aspect of the present invention is wherein the disease is fibrosis.

One aspect of the present invention is wherein the disease is steatosis.

One aspect of the present invention is wherein the disease is cirrhosis.

One aspect of the present invention is wherein the disease comprises a flavivirus disease.

One aspect of the present invention is wherein the disease is a viral disease, which impacts liver function, including but not limited to Hepatitis C. In one aspect of the present invention, the viral disease is dengue fever.

One aspect of the present invention is wherein the disease is a cystic disease, where cysts develop is tissues expressing one or more organic cation transporters, including but not limited to polycystic liver disease, polysystic ovary syndrome, or polysystic kidney disease.

One aspect of the present invention is wherein the disease is aging.

One aspect of the present invention is wherein the disease is Alzheimer's Disease.

One aspect of the present invention is wherein the disease is dementia.

One embodiment of the present invention includes use of a compound of the present invention for the preparation of a medicament for the treatment of a disease in a mammal caused by reduced activity of AMPK which comprises administration of an effective amount of a compound of the present invention.

One aspect of the present invention is wherein the disease is cancer, including but not limited to endometrial cancer, hepatocellular carcinoma, ovarian cancer, breast cancer, pancreatic cancer, colorectal cancer, lung cancer, prostate cancer, desmoplastic small round cell tumors, and renal cell carcinoma.

One aspect of the present invention is wherein the disease is one or more metabolic disorders, including but not limited to Type 2 Diabetes, pre-diabetes, hyperglycemia, Cushing disease, gestational diabetes, phenylketonuria, metabolic syndrome, syndrome X, and Tay-Sachs disease. In one embodiment, the disease is Type 2 Diabetes.

One aspect of the present invention is wherein the disease is liver disease, including but not limited to fatty liver disease.

One aspect of the present invention is wherein the disease is fibrosis.

One aspect of the present invention is wherein the disease is steatosis.

One aspect of the present invention is wherein the disease is cirrhosis.

One aspect of the present invention is wherein the disease is a flavivirus disease.

One aspect of the present invention is wherein the disease is a viral disease, which impacts liver function, including but not limited to Hepatitis C. In one aspect of the present invention, the viral disease is dengue fever.

One aspect of the present invention is wherein the disease is a cystic disease, where cysts develop is tissues expressing one or more organic cation transporters, including but not limited to polycystic liver disease, polysystic ovary syndrome, or polysystic kidney disease.

One aspect of the present invention is wherein the disease is aging.

One aspect of the present invention is wherein the disease is Alzheimer's Disease.

One aspect of the present invention is wherein the disease is dementia.

One aspect of the present invention is wherein the disease is one or more metabolic disorders, including but not limited to Type 2 Diabetes, pre-diabetes, hyperglycemia, Cushing disease, gestational diabetes, phenylketonuria, metabolic syndrome, syndrome X, and Tay-Sachs disease. In one embodiment, the disease is Type 2 Diabetes.

One aspect of the present invention is wherein the disease is fatty liver disease.

One aspect of the present invention is wherein the disease is steatosis.

One embodiment of the present invention includes a compound of the present invention for use as an active therapeutic substance.

One embodiment of the present invention includes a compound of the present invention for use in the treatment of a disease mediated by AMPK.

One aspect of the present invention is wherein the disease is cancer, including but not limited to endometrial cancer, hepatocellular carcinoma, ovarian cancer, breast cancer, pancreatic cancer, colorectal cancer, lung cancer, prostate cancer, desmoplastic small round cell tumors, and renal cell carcinoma.

One aspect of the present invention is wherein the disease is one or more metabolic disorders, including but not limited to Type 2 Diabetes, pre-diabetes, hyperglycemia, Cushing disease, gestational diabetes, phenylketonuria, metabolic syndrome, syndrome X, and Tay-Sachs disease. In one embodiment, the disease is Type 2 Diabetes.

One aspect of the present invention is wherein the disease is liver disease, including but not limited to fatty liver disease.

One aspect of the present invention is wherein the disease is fibrosis.

One aspect of the present invention is wherein the disease is steatosis.

One aspect of the present invention is wherein the disease is cirrhosis.

One aspect of the present invention is wherein the disease is a flavivirus disease.

One aspect of the present invention is wherein the disease is a viral disease, which impacts liver function, including but not limited to Hepatitis C. In one aspect of the present invention, the viral disease is dengue fever.

One aspect of the present invention is wherein the disease is a cystic disease, where cysts develop is tissues expressing one or more organic cation transporters, including but not limited to polycystic liver disease, polysystic ovary syndrome, or polysystic kidney disease.

One aspect of the present invention is wherein the disease is aging.

One aspect of the present invention is wherein the disease is Alzheimer's Disease.

One aspect of the present invention is wherein the disease is dementia.

One aspect of the present invention is wherein the disease is one or more metabolic disorders, including but not limited to Type 2 Diabetes, pre-diabetes, hyperglycemia, Cushing disease, gestational diabetes, phenylketonuria, metabolic syndrome, syndrome X, and Tay-Sachs disease. In one embodiment, the disease is Type 2 Diabetes.

One aspect of the present invention is wherein the disease is fatty liver disease.

One aspect of the present invention is wherein the disease is steatosis.

One embodiment of the present invention includes a method, use, or compound of the present invention to treat Type 2 Diabetes.

One embodiment of the present invention includes a method, use, or compound of the present invention to treat cancer, including but not limited to endometrial cancer, hepatocellular carcinoma, ovarian cancer, breast cancer, pancreatic cancer, colorectal cancer, lung cancer, prostate cancer, desmoplastic small round cell tumors, and renal cell carcinoma.

One embodiment of the present invention includes a method, use, or compound of the present invention to treat one or more metabolic disorders, including but not limited to Type 2 Diabetes, pre-diabetes, hyperglycemia, Cushing disease, gestational diabetes, phenylketonuria, metabolic syndrome, syndrome X, and Tay-Sachs disease. In one embodiment, the disease is Type 2 Diabetes.

One embodiment of the present invention includes a method, use, or compound of the present invention to treat liver disease, including but not limited to fatty liver disease.

One embodiment of the present invention includes a method, use, or compound of the present invention to treat fibrosis.

One embodiment of the present invention includes a method, use, or compound of the present invention to treat steatosis.

One embodiment of the present invention includes a method, use, or compound of the present invention to treat cirrhosis.

One embodiment of the present invention includes a method, use, or compound of the present invention to treat a flavivirus disease.

One embodiment of the present invention includes a method, use, or compound of the present invention to treat a viral disease, which impacts liver function, including but not limited to Hepatitis C.

One embodiment of the present invention includes a method, use, or compound of the present invention to treat dengue fever.

One embodiment of the present invention includes a method, use, or compound of the present invention to treat a cystic disease, where cysts develop is tissues expressing one or more organic cation transporters, including but not limited to polycystic liver disease, polysystic ovary syndrome, or polysystic kidney disease.

One embodiment of the present invention includes a method, use, or compound of the present invention to treat aging.

One embodiment of the present invention includes a method, use, or compound of the present invention to treat Alzheimer's Disease.

One embodiment of the present invention includes a method, use, or compound of the present invention to treat dementia.

One embodiment of the present invention includes a method, use, or compound of the present invention to treat fatty liver disease.

One embodiment of the present invention includes a method, use, or compound of the present invention to treat steatosis.

One aspect of the present invention includes the use of one or more compounds of formula (I) in the treatment of one or more metabolic disorders, including but not limited to Type 2 Diabetes, pre-diabetes, hyperglycemia, Cushing disease, gestational diabetes, phenylketonuria, metabolic syndrome, syndrome X, and Tay-Sachs disease. In one embodiment, the disease is Type 2 Diabetes.

Preferably, the compounds of the present invention may be used where liver-selective agents may exhibit greater potency and experience reduced renal elimination, resulting in improved efficacy, pharmacokinetics, and safety.

One aspect of the present invention includes use of one or more compounds of formula (I) in the treatment of one or more liver disease, such as disease caused by fatty liver (NASH, NAFLD), fibrosis, steatosis, or cirrhosis.

One preferred embodiment of the present invention includes a compound of formula (I) wherein Y is ethylene. One preferred embodiment of the present invention includes a compound of formula (I) wherein R1 is hydrogen.

The compounds are believed useful for the treatment of diseases and conditions caused by reduced activity of AMPK, but the invention should not be thereto limited.

The scope of the present invention includes all combinations of aspects, embodiments, and preferences herein described.

DETAILED DESCRIPTION OF THE INVENTION

Figure 1:
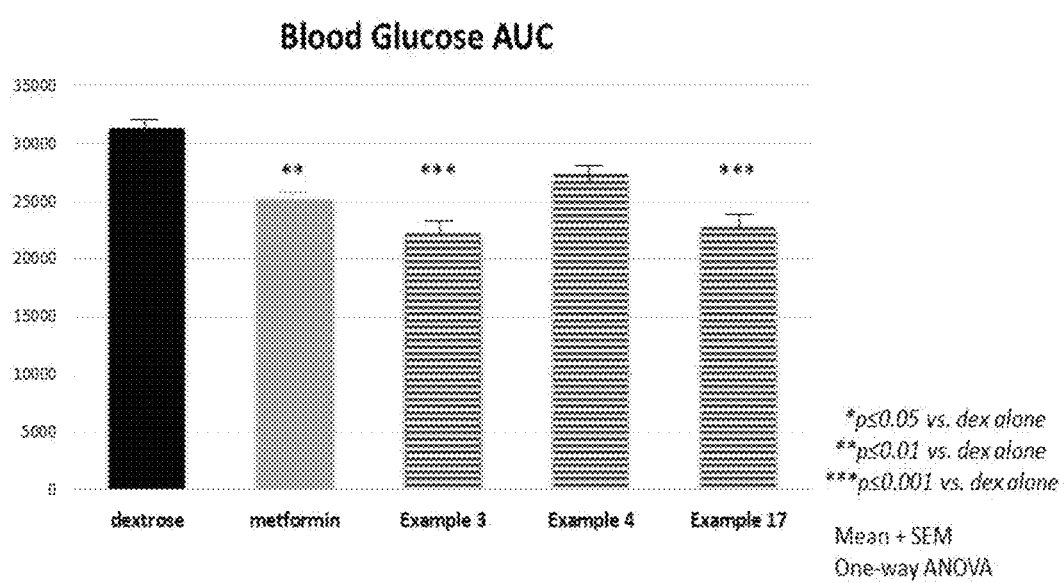
FIG. 1 is a graphic illustration of the improved effect of the compounds of the present invention on blood glucose levels.

The present invention includes novel fused bicyclic alkylene linked imidodicarbonimidic diamides according to formula I or formula II. In particular, described herein are N-[2-(indol-3-yl)alkylene]-linked imidodicarbonimidic diamides and N-[2-(pyrrolopyridin-3-yl)alkylene]-linked imidodicarbonimidic diamides (compound of formula (I) or formula (II)), which are believed to be organic cation transporter selective compounds, which are believed to be useful for the treatment of diseases and conditions caused by reduced activity of AMPK.

One hypothesis of the present inventors is that the compounds of the present invention enter cells via organic cation transporters, in particular the organic cation transporter 1 (OCT1), organic cation transporter 2 (OCT2) and organic cation transporter 3 (OCT3), and plasma membrane monoamine transporter (PMAT), and are exported by the multi-drug and toxin extrusion 1 (MATE1) transporter. The expression pattern of these transporters includes: OCT1 (predominantly liver), OCT2 (predominantly kidney), OCT3 (ubiquitous, but highly expressed in adipose tissue and skeletal muscle), PMAT (expressed in a variety of tissues including the GI tract, adipocytes and desmoplastic small round cell tumors), and MATE1 (expressed in multiple tissues, but highly prevalent in liver and kidney). Depending on the substrate specificity of a compound of formula (I), such compound can activate AMPK in a variety of cell types and have the potential to treat a variety of diseases. Herein, novel compounds are described whose activity at organic cation transporters has been optimized for activation of AMPK in tissues believed important for the treatment of metabolic disorders, including type 2 diabetes. For example, the compounds of the present invention are believed to provide enhanced exposure in tissues where activation of AMPK has a beneficial effect in the treatment of type 2 diabetes and related metabolic conditions, including metabolic syndrome or fatty liver disease. In addition, the compounds of the present invention are believed to demonstrate a reduced propensity for rapid elimination in urine, thereby offering properties of improved pharmacokinetics (PK) and a reduced risk of lactic acidosis in patients with impaired renal function.

The following definitions are meant to clarify, but not limit, the terms defined. If a particular term used herein is not specifically defined, such term should not be considered indefinite. Rather, terms are used within their accepted meanings.

As used throughout this specification, the preferred number of atoms, such as carbon atoms, will be represented by, for example, the phrase "$C_{x-y}$ alkyl," which refers to an alkyl group, as herein defined, containing the specified number of carbon atoms. Similar terminology will apply for other preferred terms and ranges as well. Thus, for example, $C_{1-4}$ alkyl represents a straight or branched chain hydrocarbon containing one to four carbon atoms.

As used herein the term "alkyl" alone or in combination with any other term, refers to a straight or branched chain hydrocarbon. Examples of "alkyl" as used herein include, but are not limited to, methyl, ethyl, propyl, isopropyl, isobutyl, n-butyl, tert-butyl, sec-butyl, isopentyl, n-pentyl, n-hexyl, and the like.

As used herein the term "alkenyl" refers to a straight or branched chain aliphatic hydrocarbon containing one or more carbon-to-carbon double bonds, which may be optionally substituted, with multiple degrees of substitution being allowed. Examples of "alkenyl" as used herein include, but are not limited to, vinyl, and allyl.

As used herein, the term "alkylene" refers to an optionally substituted straight divalent hydrocarbon radical. Examples of "alkylene" as used herein include, but are not limited to, methylene, ethylene, n-propylene, n-butylene, and the like.

As used herein the term "alkynyl" refers to a straight or branched chain aliphatic hydrocarbon containing one or more carbon-to-carbon triple bonds, which may be optionally substituted, with multiple degrees of substitution being allowed. An example of "alkynyl" as used herein includes, but is not limited to, ethynyl.

As used herein, the term "cycloalkyl" refers to a fully saturated optionally substituted monocyclic, bicyclic, or bridged hydrocarbon ring, with multiple degrees of substitution being allowed. Exemplary "cycloalkyl" groups as used herein include, but are not limited to, cyclopropyl, cyclobutyl, cyclopentyl, cyclohexyl, and cycloheptyl.

As used herein, the term "aryl" refers to a single benzene ring or fused benzene ring system which may be optionally substituted, with multiple degrees of substitution being allowed. Examples of "aryl" groups as used include, but are not limited to, phenyl, 2-naphthyl, 1-naphthyl, anthracene, and phenanthrene. Preferable aryl rings have five- to ten-members.

As used herein, a fused benzene ring system encompassed within the term "aryl" includes fused polycyclic hydrocarbons, namely where a cyclic hydrocarbon with less than maximum number of noncumulative double bonds, for example where a saturated hydrocarbon ring (cycloalkyl, such as a cyclopentyl ring) is fused with an aromatic ring (aryl, such as a benzene ring) to form, for example, groups such as indanyl and acenaphthalenyl, and also includes such groups as, for non-limiting examples, dihydronaphthalene and tetrahydronaphthalene.

As used herein, the term "heteroaryl" refers to a monocyclic five to seven membered aromatic ring, or to a fused bicyclic aromatic ring system comprising two of such aromatic rings, which may be optionally substituted, with multiple degrees of substitution being allowed. Preferably, such rings contain five- to ten-members. These heteroaryl rings contain one or more nitrogen, sulfur, and/or oxygen atoms, where N-oxides, sulfur oxides, and dioxides are permissible heteroatom substitutions. Examples of "heteroaryl" groups as used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzoxazole, benzothiophene, indole, indazole, benzimidazole, imidazopyridine, pyrazolopyridine, and pyrazolopyrimidine.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as —$CF_3$.

Typically, but not absolutely, the salts of the present invention are pharmaceutically acceptable salts. Salts encompassed within the term "pharmaceutically acceptable salts" refer to non-toxic salts of the compounds of this invention. Salts of the compound of the present invention may comprise acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

The compounds of formula (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

For use in therapy, therapeutically effective amounts of a compound of formula (I), as well as salts or solvates thereof, may be administered as the raw chemical. Additionally, the active ingredient may be presented as a pharmaceutical composition.

Accordingly, the invention further provides pharmaceutical compositions that include effective amounts of one or more compounds of the formula (I), or a salt or solvate thereof, and one or more pharmaceutically acceptable carriers, diluents, or excipients. The compound of formula (I) or a salt or solvate thereof, are as herein described. The carrier(s), diluent(s), or excipient(s) must be acceptable, in the sense of being compatible with the other ingredients of the formulation and not deleterious to the recipient of the pharmaceutical composition.

The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1999) *Protecting Groups in Organic Synthesis, 3rd Edition*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention.

The present invention also provides a method for the synthesis of compounds of formula (I) and novel compounds useful as synthetic intermediates in the preparation of compounds of the present invention.

The compounds can be prepared according to the methods described below using readily available starting materials and reagents. In these reactions, variants may be employed which are themselves known to those of ordinary skill in this art, but are not mentioned in greater detail.

Unless otherwise stated, structures depicted herein are also meant to include compounds which differ only in the presence of one or more isotopically enriched atoms. Compounds having the present structure except for the replacement of a hydrogen atom by a deuterium or tritium, or the replacement of a carbon atom by a $^{13}C$- or $^{14}C$-enriched carbon are within the scope of the invention. For example, deuterium has been widely used to examine the pharmacokinetics and metabolism of biologically active compounds. Although deuterium behaves similarly to hydrogen from a chemical perspective, there are significant differences in bond energies and bond lengths between a deuterium-carbon bond and a hydrogen-carbon bond. Consequently, replacement of hydrogen by deuterium in a biologically active compound may result in a compound that generally retains its biochemical potency and selectivity but manifests significantly different absorption, distribution, metabolism, and/or excretion (ADME) properties compared to its isotope-free counterpart. Thus, deuterium substitution may result in improved drug efficacy, safety, and/or tolerability for some biologically active compounds.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

The therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from frailty, generally, should be in the range of 0.1 to 100 mg/kg body weight of recipient (mammal) per day. More usually the effective amount should be in the range of 0.1 to 20 mg/kg body weight per day. Thus, for a 70 kg adult mammal one example of an actual amount per day would usually be from 10 to 2000 mg. This amount may be given in a single dose per day or in a number (such as two, three, four, five, or more) of sub-doses per day such that the total daily dose is the same. An effective amount of a salt or solvate thereof, may be determined as a proportion of the effective amount of the compound of formula (I) per se. Similar dosages should be appropriate for treatment of the other conditions referred to herein. Pharmaceutical formulations may be presented in unit dose forms containing a predetermined amount of active ingredient per unit dose. Such a unit may contain, as a non-limiting example, 1 mg to 2 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful certain routes will be preferable to others. In addition, pharmaceutical formulations may be used to allow delayed or extended exposure to compound of formula (I) under circumstances where delayed or extended exposure would improve therapy.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

Pharmaceutical formulations adapted for topical administration in the mouth include lozenges, pastilles, and mouthwashes.

A compound of the present invention or a salt or solvate thereof, may be employed alone or in combination with other therapeutic agents. The compound of formula (I) and the other pharmaceutically active agent(s) may be administered together or separately and, when administered separately, administration may occur simultaneously or sequentially, in any order. The amounts of the compound of formula (I) and the other pharmaceutically active agent(s) and the relative timings of administration will be selected in order to achieve the desired combined therapeutic effect. The administration in combination of a compound of formula (I) or a salt or solvate thereof with other treatment agents may be in combination by administration concomitantly in: (1) a unitary pharmaceutical composition including a combination of compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

Those skilled in the art of organic synthesis will appreciate that there exist multiple means of producing compounds of the present invention which are labeled with a radioisotope appropriate to various uses.

EXPERIMENTAL SECTION

Abbreviations

As used herein the symbols and conventions used in these processes, schemes and examples are consistent with those used in the contemporary scientific literature, for example, the Journal of the American Chemical Society or the Journal of Biological Chemistry. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| Hz (Hertz); | MHz (megahertz); |
| mol (moles); | mmol (millimoles); |
| RT or rt (room temperature); | hr (hours); |
| min (minutes); | TLC (thin layer chromatography); |
| mp (melting point); | RP (reverse phase); |
| $T_r$ (retention time); | TFA (trifluoroacetic acid); |
| TEA (triethylamine); | THF (tetrahydrofuran); |
| TFAA (trifluoroacetic anhydride); | $CD_3OD$ (deuterated methanol); |
| $CDCl_3$ (deuterated chloroform); | DMSO (dimethylsulfoxide); |
| $SiO_2$ (silica gel); | atm (atmosphere); |
| EtOAc (ethyl acetate); | $CHCl_3$ (chloroform); |
| HCl (hydrochloric acid); | Ac (acetyl); |
| DMF (N,N-dimethylformamide); | Me (methyl); |
| $Cs_2CO_3$ (cesium carbonate); | EtOH (ethanol); |
| Et (ethyl); | t-Bu (tert-butyl); |
| MeOH (methanol) | p-TsOH (p-toluenesulfonic acid); |
| DCM (dichloromethane) | DCE (dichloroethane) |
| $Et_2O$ (diethyl ether) | $K_2CO_3$ (potassium carbonate); |
| $Na_2CO_3$ (sodium carbonate); | i-PrOH (isopropyl alcohol) |
| $NaHCO_3$ (sodium bicarbonate); | ACN (acetonitrile); |
| Pr (propyl); | i-Pr (isopropyl); |
| PE (petroleum ether); | Hex (hexanes); |
| $H_2SO_4$ (sulfuric acid); | HCl (hydrochloric acid); |
| $Et_3N$ (triethylamine); | $Na_2SO_4$ (sodium sulfate); |
| MTBE (methyl tert-butyl ether); | Boc (tert-butoxycarbonyl); |
| DIPEA (diisopropylethylamine); | IPA (isopropanol); |
| HMDS (hexamethyldisilazane) | $NH_4Cl$ (ammonium chloride) |
| $NH_4CO_3$ (ammonium carbonate) | $MgSO_4$ (magnesium sulfate) |
| $NH_4OH$ (ammonium hydroxide) | |

Unless otherwise indicated, all temperatures are expressed in ° C. (degrees Centigrade). All reactions were conducted at room temperature unless otherwise noted.

H-NMR spectra were recorded on either a Bruker Fourier 600, a Varian VXR-300, or a Varian Unity-300 NMR. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad). The mass spec was run on a Sciex API 100 using electrospray ionization (ESI). The LCMS was run using a C-18 reverse phase column (2.1 ID, 3.5 micron, 50 mm). The column conditions were 98% water with 0.05% TFA and 2% MeOH to 100% MeOH over 5.5 minutes. Analytical thin layer chromatography was used to verify the purity as well as to follow the progress of reaction(s).

A compound of formula (Ib), can generally be prepared according to Scheme 1:

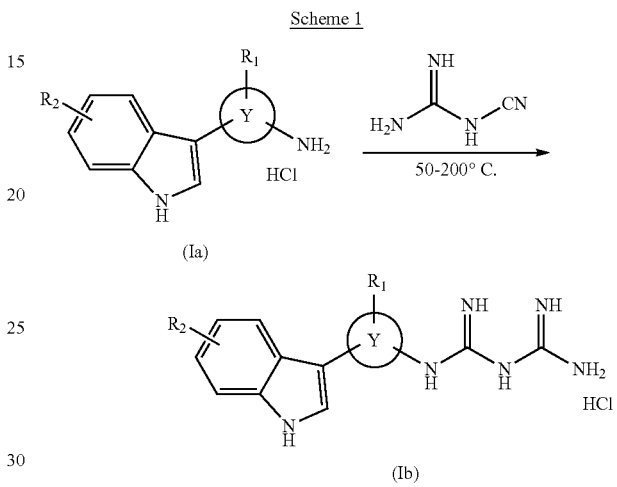

The HCl salt of formula (Ia) can be prepared from the amine as described in the literature and by methods well known to those skilled in the art.

A compound of formula (Ib), can generally be prepared according to Scheme 2:

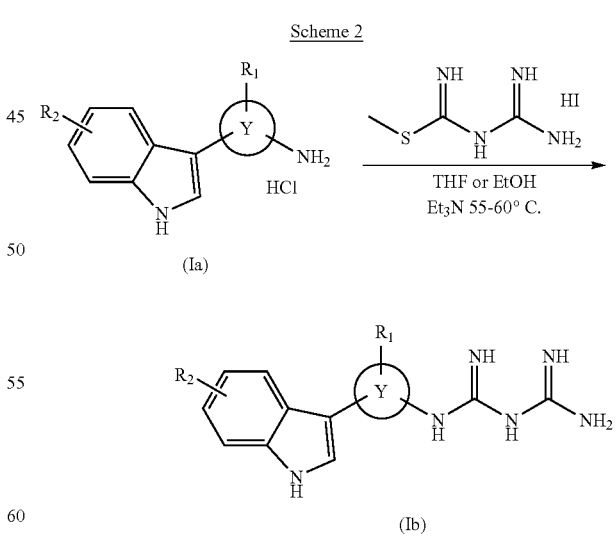

The compound of formula (Ib) can be prepared from the amine and 1-carbamimidoyl-2-methyl-isothiourea hydroiodide as described in the literature and by methods well known to those skilled in the art.

EXAMPLES

Example 1: 1-[2-(2-methyl-1H-indol-3-yl)ethyl]imidodicarbonimide diamide

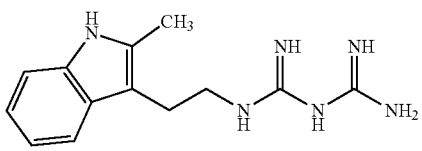 [SMILES: Cc1[nH]c2ccccc2c1CCNC(=N)NC(=N)N]

To a solution of 2-(2-methyl-1H-indol-3-yl)ethanamine (500 mg, 2.87 mmol) and dicyanamide (242 mg, 2.87 mmol) in 3.5 mL of $CH_3CN$ in a 25 mL sealed tube was added a solution of TMSCl (1.5 eq, 0.6 mL) in 0.2 mL of $CH_3CN$ dropwise at rt. The resulting mixture was stirred at 140° C. for 2 hr. After cooling to 50° C., 0.6 mL of i-PrOH was added dropwise and heating was continued at 125° C. for 30 minutes. The reaction was then cooled to rt, concentrated under vacuum, and the crude residue was purified by silica gel column chromatography (94:5:1 to 80:19:1 DCM/MeOH/NH$_3$). The desired fractions were collected, concentrated and lyophilized to obtain 1-[2-(2-methyl-1H-indol-3-yl)ethyl]imidodicarbonimide diamide as a white solid (91 mg, 12% yield). $^1$H NMR (300 MHz, $CD_3OD$) δ: 2.38 (s, 3H), 2.93 (t, J=6.9, 2H), 3.41 (t, J=9.0, 2H), 6.97 (m, 2H) 7.22 (m, 1H), 7.45 (m, 1H); LCMS calculated for $C_{13}H_{18}N_6$: m/z=258; found: m/z=259 (M+H).

Example 2: 1-[2-(5-fluoro-1H-indol-3-yl)ethyl]imidodicarbonimide diamide hydrochloride

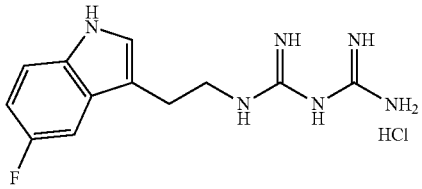 [SMILES: N=C(N)NC(=N)NCCc1c[nH]c2ccc(F)cc12 ; Cl]

Commercially available 5-fluorotryptamine hydrochloride (2.15 g, 10 mmol) and dicyandiamide (840 mg, 10 mmol) were combined in a dry pear-shaped flask under nitrogen. The contents were heated to 170° C. with stirring, with the materials forming a melt once the bath temperature was between 165-170° C. The resulting melt was heated for 3 hr then allowed to cool to rt. The contents were treated with hot MeOH-isopropanol mixture (30 mL, 1:2) and then filtered. The filtrate was concentrated, and the residue was successively treated with isopropanol (30 mL), isopropanol-acetone mixture (30 mL, 1:1), where each time the filtrate was concentrated and proceeded to next step. Finally, the residue was treated with hot isopropanol-EtOAc mixture (40 mL, 1:1) to dissolve the material, which was then precipitated with excess $Et_2O$ to obtain 740 mg (25% yield) of 1-[2-(5-fluoro-1H-indol-3-yl)ethyl]imidodicarbonimide diamide hydrochloride. $^1$H NMR (600 MHz, DMSO-d$_6$) δ 2.86 (t, J=7.3, 2H) 3.39 (m, 2H) 6.13 (s, br, 1H) 6.58-6.98 (m, 3H) 7.09 (s, br, 1H) 7.19-7.57 (m, 4H) 7.65 (s, br 1H) 11.07 (s, br 1H); LCMS calculated for $C_{12}H_{15}FN_6$: m/z=262; found: m/z=263 (M+H).

Example 3: 1-[2-(7-fluoro-1H-indol-3-yl)ethyl]imidodicarbonimide diamide

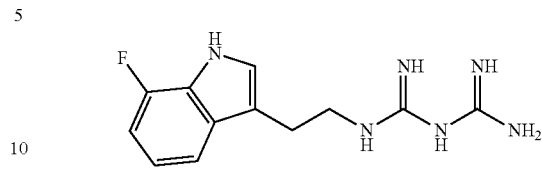

To a solution of 2-(7-fluoro-1H-indol-3-yl)ethan-1-amine (167 mg, 0.93 mmol) and dicyandiamide (78 mg, 0.93 mmol) in 1.2 mL of $CH_3CN$ in a 25 mL sealed tube was added a solution of TMSCl (1.5 eq., 0.2 mL) in 0.5 mL of $CH_3CN$ dropwise at rt. The resulting mixture was stirred and heated to 140° C. for 2 hr. After cooling to 50° C., 0.2 mL of isopropanol was added dropwise and the reaction mixture was heated to 125° C. for 30 min. The reaction was cooled to rt and the volatiles were removed under vacuum. Purification of the crude reaction mixture by silica gel chromatography using a gradient elution (94:5:1 to 80:19:1 DCM/MeOH/NH$_3$) afforded 1-[2-(7-fluoro-1H-indol-3-yl)ethyl]imidodicarbonimide diamide as a white solid (57 mg, 23% yield). $^1$H NMR (300 MHz, $CD_3OD$) δ 3.01 (m, 2H) 3.52 (m, 2H), 6.82 (m, 1H), 6.95 (m, 1H), 7.18 (m, 1H), 7.36 (m, 1H); LCMS calculated for $C_{12}H_{15}FN_6$: m/z=262; found: m/z=263 (M+H).

Example 4: 1-[2-(5-fluoro-1-methyl-1H-indol-3-yl)ethyl]imidodicarbonimide diamide

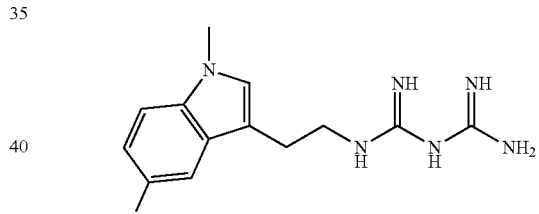

Step 1: tert-butyl (2-(5-fluoro-1H-indol-3-yl)ethyl)carbamate

To a solution of 2-(5-fluoro-1H-indol-3-yl)ethan-1-amine (1.0 g, 4.7 mmol) in 1,4-dioxane (10 mL) was added di-tert-butyl dicarbonate (1.6 g, 7.3 mmol). The reaction mixture was stirred at rt for 16 hr, then concentrated under vacuum. Purification of the crude reaction mixture by silica gel chromatography (30% EtOAc in hexanes) afforded tert-butyl (2-(5-fluoro-1H-indol-3-yl)ethyl)carbamate as a pale yellow solid (1.3 g, 99% yield).

Step 2: tert-butyl (2-(5-fluoro-1-methyl-1H-indol-3-yl)ethyl)carbamate

To a solution of tert-butyl (2-(5-fluoro-1H-indol-3-yl)ethyl)carbamate (1.3 g, 4.6 mmol) in anhydrous THF (15 mL) at 0° C. was added NaH (250 mg, 6.11 mmol, 60% in mineral oil). The resulting reaction mixture was warmed to rt and stirred 15 min, then iodomethane (800 mg, 5.64 mmol) in THF (5 mL) was added dropwise. The resulting reaction mixture was stirred at rt for 3 hrs, then quenched by careful addition of saturated aqueous ammonium chloride (10 mL). The reaction mixture was diluted with EtOAc (40 mL) and washed with brine (30 mL). The organic layer was separated, dried over anhydrous $Na_2SO_4$, filtered and the solvents removed under vacuum. Purification by silica gel chromatography (20% EtOAc in hexanes) afforded tert-butyl (2-(5-fluoro-1-methyl-1H-indol-3-yl)ethyl)carbamate as a yellow solid (900 mg, 66% yield).

Step 3: 2-(5-fluoro-1-methyl-1H-indol-3-yl)ethan-1-amine

To a solution of tert-butyl (2-(5-fluoro-1-methyl-1H-indol-3-yl)ethyl)carbamate (1.29 g, 4.71 mmol) in DCM (15 mL) at 0° C. was added TFA (7 mL). The resulting reaction mixture was warmed to rt and stirred 1 hr. The reaction mixture was concentrated under vacuum to give the crude product, which was diluted with DCM (20 mL) and washed with aqueous $NaHCO_3$ (15 mL) then brine (15 mL). The organic layer was separated, dried over anhydrous $Na_2SO_4$, filtered and the solvents removed under vacuum to afford 2-(5-fluoro-1-methyl-1H-indol-3-yl)ethan-1-amine as a yellow oil (540 mg, 91% yield). $^1$H NMR (300 MHz, $CD_3OD$) δ 3.04-3.39 (m, 4H), 3.76 (s, 3H), 6.95 (m, 1H), 7.17 (s, 1H), 7.29 (m, 2H).

Step 4: 1-[2-(5-fluoro-1-methyl-1H-indol-3-yl)ethyl]imidodicarbonimide Diamide

To a solution of 2-(5-fluoro-1-methyl-1H-indol-3-yl)ethan-1-amine (100 mg, 0.52 mmol) and dicyandiamide (44 mg, 0.52 mmol) in 0.4 mL of $CH_3CN$ in a 25 mL sealed tube was added a solution of TMSCl (1.5 eq., 0.1 mL) in 0.4 mL of $CH_3CN$ dropwise at rt. The resulting mixture was stirred and heated to 140° C. for 2 hr. After cooling to 50° C., 0.1 mL of isopropanol was added dropwise and the reaction mixture was heated to 125° C. for 30 min. The reaction was cooled to rt and the volatiles were removed under vacuum. Purification of the crude reaction mixture by silica gel chromatography using a gradient elution (94:5:1 to 80:19:1 $DCM/MeOH/NH_3$) afforded 1-[2-(5-fluoro-1-methyl-1H-indol-3-yl)ethyl]imidodicarbonimide diamide as a white solid (44 mg, 31% yield). $^1$H NMR (300 MHz, $CD_3OD$) δ 3.00 (m, 2H) 3.55 (m, 2H), 3.76 (s, 3H), 6.93 (dt, J=8.1, 21.2, 1H), 7.13 (s, br, 1H), 7.25 (m, 2H); LCMS calculated for $C_{13}H_{17}FN_6$: m/z=276; found: m/z=277 (M+H).

Example 5: 1-[1-(5-fluoro-1H-indol-3-yl)propan-2-yl]imidodicarbonimide diamide

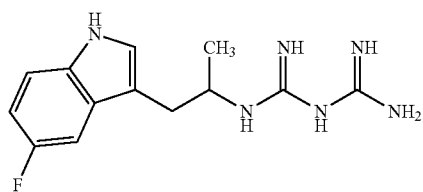 [SMILES: CC(Cc1c[nH]c2ccc(F)cc12)NC(=N)NC(=N)N]

Step 1: 5-fluoro-3-(2-nitroprop-1-en-1-yl)-1H-indole

A solution of 5-fluoro-1H-indole-3-carbaldehyde (50 g, 0.28 mol) and ammonium acetate (1.6 g, 23.5 mmol) in nitroethane (500 mL) was refluxed for 2 hr. The reaction mixture was concentrated under vacuum to remove the nitroethane, then diluted with EtOAc (200 mL) and washed with water (1×200 mL), brine (1×200 mL) and dried over anhydrous $Na_2SO_4$. The reaction mixture was filtered and the solvent removed under vacuum. The crude product was precipitated from a solution of 30% EtOAc in hexanes to provide 5-fluoro-3-(2-nitroprop-1-en-1-yl)-1H-indole as a brown solid. $^1$H NMR (300 MHz, DMSO-$d_6$) δ 2.46 (s, 3H), 7.07 (m, 1H), 7.48 (m, 1H), 7.67 (m, 1H), 8.05 (s, 1H), 8.39 (s, 1H), 12.20 (s, 1H).

Step 2: 1-(5-fluoro-1H-indol-3-yl)propan-2-amine Hydrochloride

A solution of 5-fluoro-3-(2-nitroprop-1-en-1-yl)-1H-indole (2 g, 9.08 mmol) in anhydrous THF (20 mL) was added dropwise to a suspension of $LiAlH_4$ (1.4 g, 36.16 mmol) in anhydrous THF at 0° C. The resulting reaction mixture was then heated to reflux for 2 hrs. The reaction mixture was cooled to 0° C. and quenched by careful dropwise addition of brine. The reaction mixture was diluted with EtOAc (50 mL) and filtered through a pad of celite. The filtrate was dried over anhydrous $Na_2SO_4$, filtered and the solvents removed under vacuum to afford a viscous brown oil. Purification by silica gel chromatography using a gradient elution (94:5:1 to 80:19:1 $DCM/MeOH/NH_3$) afforded 1-(5-fluoro-1H-indol-3-yl)propan-2-amine as the free base. This material was dissolved in 5 mL of 1,4-dioxane, cooled to 0° C., and treated with 10 mL of 4N HCl in 1,4-dioxane. The resulting solution was stirred 30 min at rt then the solvents were removed under vacuum and the resulting brown solid was dried under high vacuum to afford 1-(5-fluoro-1H-indol-3-yl)propan-2-amine hydrochloride (1.0 g). $^1$H NMR (300 MHz, $CD_3OD$) δ 1.11 (d, J=6.3, 3H), 2.71 (m, 2H), 2.64-2.80 (m, 1H), 6.85 (m, 1H), 7.20 (m, 2H), 7.28 (m, 1H); LCMS calculated for $C_{11}H_{13}FN_2$: m/z=192; found: m/z=193 (M+H).

Step 3: 1-[1-(5-fluoro-1H-indol-3-yl)propan-2-yl]imidodicarbonimide diamide

A mixture of 1-(5-fluoro-1H-indol-3-yl)propan-2-amine hydrochloride (270 mg, 1.40 mmol) and dicyandiamide (118 mg, 1.40 mmol) in 2 mL of $CH_3CN$ in a 25 mL sealed tube was added a solution of TMSCl (1.5 eq., 0.3 mL) in 1 mL of $CH_3CN$ dropwise at rt. The resulting mixture was stirred and heated to 140° C. for 2 hr. After cooling to 50° C., 0.3 mL of isopropanol was added dropwise and the reaction mixture was heated to 125° C. for 30 min. The reaction was cooled to rt and the volatiles were removed under vacuum. Purification of the crude reaction mixture by silica gel chromatography using a gradient elution (94:5:1 to 80:19:1 $DCM/MeOH/NH_3$) afforded to afford 1-[1-(5-fluoro-1H-indol-3-yl)propan-2-yl]imidodicarbonimide diamide as a white solid (67 mg, 17% yield). $^1$H NMR (300 MHz, $CD_3OD$) δ 1.17 (d, J=6.9, 3H), 2.89 (m, 2H), 4.12 (s, br, 1H), 6.84 (m, 1H), 7.14 (s, 4H), 7.27 (m, 2H); LCMS calculated for $C_{13}H_{17}FN_6$: m/z=276; found: m/z=277 (M+H).

Example 6: 1-[1-(5-fluoro-1-methyl-1H-indol-3-yl)propan-2-yl]imidodicarbonimide Diamide

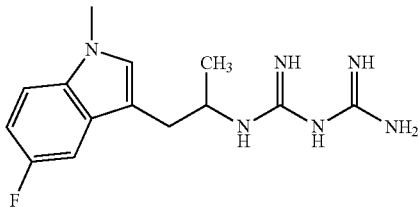 [SMILES: CC(Cc1cn(C)c2ccc(F)cc12)NC(=N)NC(=N)N]

Step 1: tert-butyl (1-(5-fluoro-1H-indol-3-yl)propan-2-yl)carbamate

To a solution of 1-(5-fluoro-1H-indol-3-yl)propan-2-amine (1.4 g, 7.3 mmol) in 1,4-dioxane (10 mL) was added di-tert-butyl dicarbonate (2.7 g, 11 mmol). The reaction mixture was stirred at rt for 16 hr, then concentrated under vacuum. Purification of the crude reaction mixture by silica gel chromatography (20% EtOAc in hexanes) tert-butyl (1-(5-fluoro-1H-indol-3-yl)propan-2-yl)carbamate as a yellow solid (1.73 g, 81% yield). $^1$H NMR (300 MHz, CDCl$_3$) δ 1.12 (d, J=6.6, 3H), 1.42 (s, 9H), 2.85 (m, 2H), 3.98 (s, br, 1H), 4.42 (m, 1H), 6.93 (m, 1H), 7.05 (d, J=2.4, 1H), 7.27 (m, 2H), 8.10 (s, br, 1H).

Step 2: tert-butyl (1-(5-fluoro-1-methyl-1H-indol-3-yl)propan-2-yl)carbamate To a solution of tert-butyl (1-(5-fluoro-1H-indol-3-yl)propan-2-yl) carbamate (1.7 g, 5.8 mmol) in anhydrous THF (15 mL) at 0° C. was added NaH (308 mg, 7.41 mmol, 60% in mineral oil). The resulting reaction mixture was warmed to rt and stirred 15 min, then iodomethane (988 mg, 6.96 mmol) in THF (5 mL) was added dropwise. The resulting reaction mixture was stirred at rt for 3 hrs, then quenched by careful addition of saturated aqueous ammonium chloride (10 mL). The reaction mixture was diluted with EtOAc (50 mL) and washed with brine (30 mL). The organic layer was separated, dried over anhydrous Na$_2$SO$_4$, filtered and the solvents removed under vacuum. Purification by silica gel chromatography (20% EtOAc in hexanes) afforded tert-butyl (1-(5-fluoro-1-methyl-1H-indol-3-yl)propan-2-yl)carbamate as a brown solid (1.4 g, 79% yield).

Step 3: 1-(5-fluoro-1-methyl-1H-indol-3-yl)propan-2-amine

To a solution of tert-butyl (1-(5-fluoro-1-methyl-1H-indol-3-yl)propan-2-yl)carbamate (1.4 g, 4.5 mmol) in DCM (50 mL) at 0° C. was added TFA (15 mL). The resulting reaction mixture was warmed to rt and stirred 1 hr. The reaction mixture was concentrated under vacuum to give the crude product, which was diluted with DCM (20 mL) and washed with aqueous NaHCO$_3$ (15 mL) then brine (15 mL). The organic layer was separated, dried over anhydrous Na$_2$SO$_4$, filtered and the solvents removed under vacuum to afford 1-(5-fluoro-1-methyl-1H-indol-3-yl)propan-2-amine as a yellow oil (750 mg, 81% yield). $^1$H NMR (300 MHz, CD$_3$OD) δ 1.15 (d, J=6.3, 3H), 2.77 (t, J=5.4, 2H), 3.23 (m, 1H), 3.75 (s, 3H), 6.91 (m, 1H), 7.07 (s, 1H), 7.24 (m, 2H).

Step 4: 1-[1-(5-fluoro-1-methyl-1H-indol-3-yl)propan-2-yl]imidodicarbonimide diamide To a solution of 1-(5-fluoro-1-methyl-1H-indol-3-yl)propan-2-amine (200 mg, 0.97 mmol) and dicyandiamide (82 mg, 0.97 mmol) in 1.3 mL of CH$_3$CN in a 25 mL sealed tube was added a solution of TMSCl (1.5 eq., 0.2 mL) in 0.8 mL of CH$_3$CN dropwise at rt. The resulting mixture was stirred and heated to 140° C. for 2 hr. After cooling to 50° C., 0.2 mL of isopropanol was added dropwise and the reaction mixture was heated to 125° C. for 30 min. The reaction was cooled to rt and the volatiles were removed under vacuum. Purification of the crude reaction mixture by silica gel chromatography using a gradient elution (94:5:1 to 80:19:1 DCM/MeOH/NH$_3$) afforded 1-[1-(5-fluoro-1-methyl-1H-indol-3-yl)propan-2-yl]imidodicarbonimide diamide as a white solid (125 mg, 45% yield). $^1$H NMR (300 MHz, CD$_3$OD) δ 1.17 (d, J=6.6, 3H), 2.89 (m, 2H) 4.10 (s, br, 1H), 3.75 (s, 3H), 6.91 (m, 1H), 7.07 (s, 1H), 7.27 (m, 2H); LCMS calculated for C$_{14}$H$_{19}$FN$_6$: m/z=290; found: m/z=291 (M+H).

Example 7: 1-[2-(1H-indol-3-yl)propyl]imidodicarbonimide diamide hydrochloride

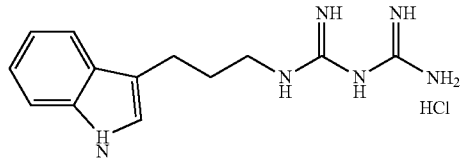 [SMILES: N=C(N)NC(=N)NCCCc1c[nH]c2ccccc12 ; Cl]

Commercially available 1H-indol-3-ylpropanamine HCl (420 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtered solids were isolated then triturated with acetone, filtered, isolated, and dried under vacuum to afford 1-[2-(1H-indol-3-yl)propyl]imidodicarbonimide diamide hydrochloride (120 mg, 20% yield) as a white solid. $^1$H NMR (600 MHz, DMSO-d$_6$) δ 1.95 (d, J=7.3, 2H), 2.81 (m, 2H), 3.16 (d, J=6.2, 2H), 6.72-7.20 (m, 7H), 7.34 (t, J=7.2, 2H), 7.53 (d, J=7.3, 1H), 8.03 (s, br, 1H), 10.83 (s, br, 1H); LCMS calculated for C$_{13}$H$_{18}$N$_6$: m/z=258; found: m/z=259 (M+H).

Example 8: 1-[2-(1H-indol-3-yl)-2-methylpropyl)-3-methyl]imidodicarbonimide diamide

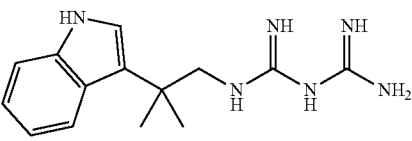 [SMILES: CC(C)(CNC(=N)NC(=N)N)c1c[nH]c2ccccc12]

To a solution of 2-(1H-indol-3-yl)-2-methylpropan-1-amine (200 mg, 1.06 mmol) and dicyandiamide (90 mg, 1.06 mmol) in 1.4 mL of CH$_3$CN in a 25 mL sealed tube was added a solution of TMSCl (1.5 eq., 0.2 mL) in 0.4 mL of CH₃CN dropwise at rt. The resulting mixture was stirred and heated to 140° C. for 2 hr. After cooling to 50° C., 0.2 mL of isopropanol was added dropwise and the reaction mixture was heated to 125° C. for 30 min. The reaction was cooled to rt and the volatiles were removed under vacuum. Purification of the crude reaction mixture by silica gel chromatography using a gradient elution (94:5:1 to 80:19:1 DCM/MeOH/NH₃) afforded 1-[1-(1H-indol-3-yl)-2-methylpropan-2-yl]imidodicarbonimide diamide hydrochloride as a white solid (114 mg, 50% yield). ¹H NMR (300 MHz, CD₃OD) δ 1.45 (s, 6H), 4.79 (s, 2H), 6.99-7.08 (m, 3H), 7.35 (d, J=7.2 Hz, 1H), 7.72 (d, J=8.1, 1H); LCMS calculated for $C_{14}H_{20}N_6$: m/z=272; found: m/z=273 (M+H).

Example 9: 1-[2-(5-chloro-1H-indol-3-yl)ethyl]imidodicarbonimide diamide, trifluoroacetic acid salt

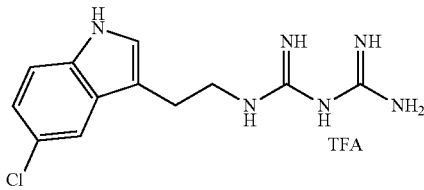 [SMILES: N=C(N)NC(=N)NCCc1c[nH]c2ccc(Cl)cc12]

Commercially available 2-(5-chloro-1H-indol-3-yl)ethan-1-amine HCl (388 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H₂O (2-3 mL), and purified by reverse phase semi-preparative HPLC eluting with gradient of H₂O-MeOH (Mobile Phase A: H₂O (0.05% TFA); Mobile Phase B: MeOH (0.05% TFA)) for 30 minutes. Mobile Phase B is 0% at the start and reaches 100% at 20 minutes and maintained until t=30 minutes) to afford 35 mg (6%) of 1-[2-(5-chloro-1H-indol-3-yl)ethyl]imidodicarbonimide diamide trifluoroacetic acid salt as a white solid. ¹H NMR (600 MHz, DMSO-d₆) δ 2.84 (m, 2H), 3.34 (m, 2H), 6.68-7.08 (m, 4H), 7.12-7.46 (m, 5H), 7.57 (s, br, 1H), 11.08 (s, br 1H); LCMS calculated for $C_{12}H_{15}ClN_6$: m/z=278; found: m/z=280 (M+H).

Example 10: 1-[2-(5-methyl-1H-indol-3-yl)ethyl]imidodicarbonimide diamide trifluoroacetic acid salt

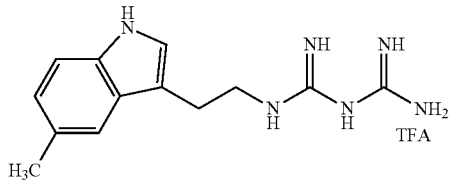 [SMILES: Cc1ccc2[nH]cc(CCNC(=N)NC(=N)N)c2c1]

Commercially available 2-(5-methyl-1H-indol-3-yl)ethan-1-amine HCl (350 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H₂O (2-3 mL), and purified by reverse phase semi-preparative HPLC eluting with gradient of H₂O-MeOH (Mobile Phase A: H₂O (0.05% TFA); Mobile Phase B: MeOH (0.05% TFA)) for 30 minutes. Mobile Phase B is 0% at the start and reaches 100% at 20 minutes and maintained until t=30 minutes) to afford 25 mg (5%) of 1-[2-(5-methyl-1H-indol-3-yl)ethyl]imidodicarbonimide diamide trifluoroacetic acid salt as an off-white solid. ¹H NMR (600 MHz, DMSO-d₆) δ 2.34 (s, 3H), 2.84 (t, J=7.2, 2H), 3.35 (m, 2H) 6.63-6.96 (m, 3H), 7.09 (s, 2H), 7.15-7.35 (m, 4H), 7.40 (s, br, 1H), 10.72 (s, br, 1H); LCMS calculated for $C_{13}H_{18}N_6$: m/z=258; found: m/z=259 (M+H).

Example 11: 1-[2-(6-fluoro-1H-indol-3-yl)ethyl] imidodicarbonimide Diamide Trifluoroacetic Acid Salt

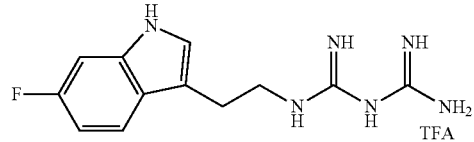 [SMILES: N=C(N)NC(=N)NCCc1c[nH]c2cc(F)ccc12]

Commercially available 2-(6-fluoro-1H-indol-3-yl)ethan-1-amine HCl (356 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H₂O (2-3 mL), and purified by reverse phase semi-preparative HPLC eluting with gradient of H₂O-MeOH (Mobile Phase A: H₂O (0.05% TFA); Mobile Phase B: MeOH (0.05% TFA)) for 30 minutes. Mobile Phase B is 0% at the start and reaches 100% at 20 minutes and maintained until t=30 minutes) to afford 35 mg (11%) of 1-[2-(6-fluoro-1H-indol-3-yl)ethyl]imidodicarbonimide diamide trifluoroacetic acid salt as an off-white solid. ¹H NMR (600 MHz, DMSO-d₆) δ 2.85 (t, J=7.2 Hz, 2H), 3.28-3.40 (m, 2H), 6.52-6.97 (m, 3H), 7.01-7.22 (m, 3H), 7.23-7.64 (m, 4H), 10.96 (s, br 1H); LCMS calculated for $C_{12}H_{15}FN_6$: m/z=262; found: m/z=263 (M+H).

Example 12: 1-[2-(5-ethoxy-1H-indol-3-yl)ethyl] imidodicarbonimide diamide trifluoroacetic acid salt

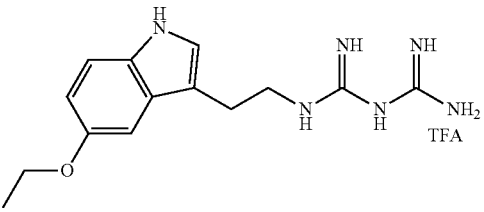 [SMILES: CCOc1ccc2[nH]cc(CCNC(=N)NC(=N)N)c2c1]

Commercially available 2-(5-ethoxy-1H-indol-3-yl)ethan-1-amine HCl (480 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 20 mg (4%) of 1-[2-(5-ethoxy-1H-indol-3-yl)ethyl]imidodicarbonimide diamide trifluoroacetic acid salt as an off-white solid. $^1$H NMR (Bruker, 600 MHz, DMSO-d$_6$) δ ppm 1.29 (t, J=5.85, 3H), 2.83 (s, br, 2H), 3.31-3.46 (m, 2H), 3.98 (s, br, 2H), 6.69 (s, br, 3H), 6.97 (s, br, 2H), 7.09 (s, br, 2H), 7.14-7.27 (m, 2H), 7.38 (s, br, 2H), 10.64 (s, br, 1H); LCMS calculated for C$_{14}$H$_{20}$N$_6$O: m/z=288; found: m/z=289 (M+H).

Example 13: 1-[2-(1-(2-hydroxyethyl)-1H-indol-3-yl)ethyl]imidodicarbonimide diamide trifluoroacetic acid salt

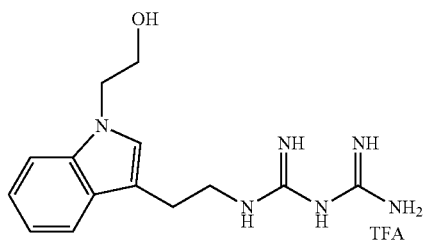 [SMILES: N=C(N)NC(=N)NCCc1cn(CCO)c2ccccc12]

Commercially available 2-(3-(2-aminoethyl)-1H-indol-1-yl)ethan-1-ol hydrochloride (480 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 25 mg (8%) of 1-[2-(1-(2-hydroxyethyl)-1H-indol-3-yl)ethyl]imidodicarbonimide diamide hydrochloride as an off-white solid. $^1$H NMR (600 MHz, DMSO-d$_6$) δ 2.86 (t, J=7.17, 2H), 3.38 (s, br, 2H), 3.67 (s, br 2H), 4.12 (s, br, 2H), 4.78 (s, br 1H), 6.98 (s, br 2H), 7.09 (m, 2H), 7.17 (s, br, 2H), 7.38 (s, br, 3H), 7.51 (s, br, 2H); LCMS calculated for C$_{14}$H$_{20}$N$_6$O: m/z=288; found: m/z=289 (M+H).

Example 14: 1-[2-(4-methoxy-1H-indol-3-yl)ethyl]imidodicarbonimide diamide trifluoroacetic acid salt

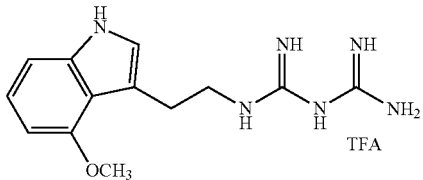 [SMILES: COc1cccc2[nH]cc(CCNC(=N)NC(=N)N)c12]

Commercially available 2-(4-methoxy-1H-indol-3-yl)ethan-1-amine HCl (450 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 40 mg (13%) of 1-[2-(4-methoxy-1H-indol-3-yl)ethyl]imidodicarbonimide diamide trifluoroacetic acid salt as an off-white solid. $^1$H NMR (Bruker, 600 MHz, DMSO-d$_6$) δ 2.95 (s, br, 2H), 3.03 (m, 1H), 3.13 (s, br, 1H), 3.81 (s, 3H), 6.42 (s, br, 2H), 6.63-7.18 (m, 8H), 10.76 (s, br, 1H); LCMS calculated for C$_{13}$H$_{18}$N$_6$O: m/z=274; found: m/z=275 (M+H).

Example 15: 1-(2-(5-(2-hydroxyethoxy)-1H-indol-3-yl)ethyl)imidodicarbonimide diamide trifluoroacetic acid salt

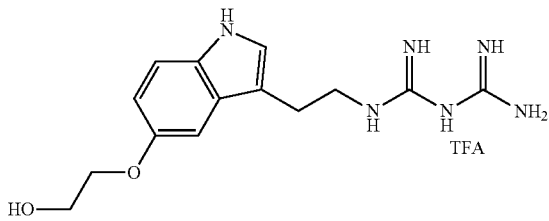 [SMILES: N=C(N)NC(=N)NCCc1c[nH]c2ccc(OCCO)cc12]

Commercially available 2-(3-(2-aminoethyl)-1H-indol-5-yl)oxy)ethan-1-ol hydrochloride (510 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 35 mg (10%) of 1-(2-(5-(2-hydroxyethoxy)-1H-indol-3-yl)ethyl)imidodicarbonimide diamide trifluoroacetic acid salt as an off-white solid. $^1$H NMR (Bruker, 600 MHz, DMSO-d$_6$) δ 2.83 (t, J=7.0, 2H), 2.89 (t, J=7.7, 1H), 3.01 (s, br, 1H), 3.69 (t, J=4.8, 2H), 3.95 (t, J=5.0, 2H), 6.57-6.90 (m, 4H), 6.96 (m, 2H), 7.04-7.24 (m, 3H), 7.39 (s, br, 1H), 7.70 (s, br, 1H); LCMS calculated for C$_{14}$H$_{20}$N$_6$O$_2$: m/z=304; found: m/z=305 (M+H).

Example 16: 1-[2-(1,2-dimethyl-1H-indol-3-yl)ethyl]imidodicarbonimide diamide

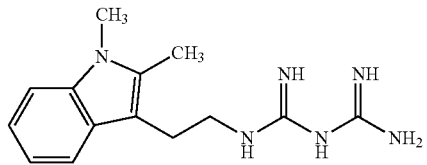 [SMILES: Cc1c(CCNC(=N)NC(=N)N)c2ccccc2n1C]

Step 1: tert-Butyl (2-(2-methyl-1H-indol-3-yl)ethyl)carbamate

To a solution of 2-(2-methyl-1H-indol-3-yl)ethanamine (272 mg, 1.55 mmol) in 1,4-dioxane (5 mL) was added di-tert-butyl dicarbonate (500 mg, 2.3 mmol). The resulting reaction mixture was stirred at rt for 16 hr. The mixture was concentrated to give the crude product, which was purified by silica gel column chromatography (20% EtOAc in hexanes) to afford tert-butyl (2-(2-methyl-1H-indol-3-yl)ethyl)carbamate (382 mg, 1.4 mmol, 90% yield) as a pale yellow oil.

Step 2: tert-Butyl (2-(1,2-dimethyl-1H-indol-3-yl)ethyl)carbamate

To a solution of tert-butyl (2-(2-methyl-1H-indol-3-yl)ethyl)carbamate (382 mg, 1.4 mmol) in anhydrous THF (15 mL) was added sodium hydride (73 mg, 1.8 mmol, 60% in mineral oil) at 0° C. under nitrogen. After the resulting reaction mixture was stirred at rt for 15 min, the reaction was cooled to 0° C. and iodomethane (240 mg, 1.7 mmol) in THF (5 mL) was added dropwise. The resulting mixture was warmed to rt and stirred for 3 h, then quenched with saturated aqueous ammonium chloride solution (10 mL). The aqueous layer was extracted with EtOAc (2×15 mL). The combined organic layers were washed with brine, dried over Na$_2$SO$_4$, filtered and concentrated under vacuum. The crude product was purified by silica gel column chromatography (20% EtOAc in Hexane) to afford tert-butyl (2-(1,2-dimethyl-1H-indol-3-yl)ethyl)carbamate (300 mg, 75% yield) as a yellow solid.

Step 3: 2-(1,2-dimethyl-1H-indol-3-yl)ethanamine

To a solution of tert-butyl (2-(1,2-dimethyl-1H-indol-3-yl)ethyl)carbamate (220 mg, 0.76 mmol) in DCM (10 mL) was added TFA (5 mL) at 5° C. The resulting reaction mixture was warmed to rt and stirred for 1 hr. The reaction mixture was concentrated to give the crude product which was diluted with 15 mL of DCM and washed with aqueous NaHCO$_3$ (2×15 mL). The organic layer was washed with brine, dried and concentrated to give 2-(1,2-dimethyl-1H-indol-3-yl)ethanamine (140 mg, 69% yield) as yellow oil. $^1$H NMR (300 MHz, CD$_3$OD) δ: 2.37 (s, 3H), 2.84 (m, 4H), 3.65 (s, 3H), 6.96 (m, 1H), 7.07 (m, 1H), 7.25 (d, 1H, J=8.1, 1H), 7.45 (d, J=7.8, 1H).

Step 4: 1-[2-(1,2-dimethyl-1H-indol-3-yl)ethyl]imidodicarbonimide diamide

To a solution of 2-(1,2-dimethyl-1H-indol-3-yl)ethanamine (140 mg, 0.75 mmol) and dicyanamide (63 mg, 0.75 mmol) in 1 mL of CH$_3$CN in a 25 mL sealed tube was added a solution of TMSCl (1.5 eq, 0.15 mL) in 0.5 mL of CH$_3$CN dropwise at rt. The resulting mixture was stirred at 140° C. for 2 hr. After cooling to 50° C., 0.15 mL of i-PrOH was added dropwise and heating was continued at 125° C. for 30 minutes. The reaction was then cooled to rt and concentrated under vacuum. The crude residue was purified by silica gel column chromatography (94:5:1 to 80:19:1 DCM/MeOH/NH$_3$). The desired fractions were collected, concentrated and lyophilized to obtain 1-[2-(1,2-dimethyl-1H-indol-3-yl)ethyl]imidodicarbonimide diamide as a white solid (75 mg, 37% yield). $^1$H NMR (300 MHz, CD$_3$OD) δ: 2.38 (s, 3H), 2.95 (t, J=7.2, 2H), 3.42 (t, J=7.2, 2H), 3.65 (s, 3H), 6.99-7.10 (m, 2H), 7.26 (d, J=7.8, 1H), 7.48 (d, J=7.2, 1H); LCMS calculated for C$_{14}$H$_{20}$N$_6$: m/z=272; found: m/z=273 (M+H).

Example 17: 1-[2-(1H-indol-3-yl)ethyl]imidodicarbonimide diamide hydrochloride

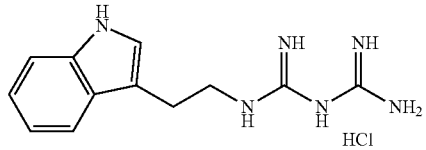 [SMILES: N=C(N)NC(=N)NCCc1c[nH]c2ccccc12 ; Cl]

Commercially available 2-(1H-indol-3-yl)ethan-1-amine hydrochloride (380 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The crude material was triturated with 30 mL of isopropanol, filtered, then triturated with 30 mL of acetone, filtered, and dried to give 1-[2-(1H-indol-3-yl)ethyl]imidodicarbonimide diamide hydrochloride (200 mg, 38% yield) as a cream solid. $^1$H NMR (600 MHz, DMSO-d$_6$) δ 2.86 (t, J=6.7, 2H), 3.39 (m, 2H), 6.86-7.13 (m, 7H), 7.18 (s, br 1H), 7.31 (d, J=8.2, 2H), 7.50 (d, J=7.6, 1H), 7.59 (m, 1H), 10.90 (s, br, 1H); LCMS calculated for C$_{12}$H$_{16}$N$_6$: m/z=244; found: m/z=245 (M+H).

Example 18: 1-[2-(5-nitro-1H-indol-3-yl)ethyl]imidodicarbonimide diamide, trifluoroacetic acid salt

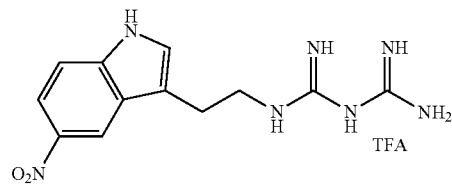 [SMILES: N=C(N)NC(=N)NCCc1c[nH]c2ccc([N+](=O)[O-])cc12 ; "TFA"]

Commercially available 2-(5-nitro-1H-indol-3-yl)ethan-1-amine HCl (440 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 25 mg (4%) of 1-[2-(5-nitro-1H-indol-3-yl)ethyl]imidodicarbonimide diamide trifluoroacetic acid salt as a white solid. $^1$H NMR (600 MHz, DMSO-d$_6$) δ 2.94 (s, br, 2H), 3.37 (s, br, 2H), 6.84 (s, br, 5H) 7.41 (s, br, 3H) 7.73 (s, br 1H) 7.94 (s, br, 1H) 8.52 (s, br, 1H) 11.59 (s, br 1H); LCMS calculated for C$_{12}$H$_{15}$N$_7$O$_2$: m/z=289; found: m/z=290 (M+H).

Example 19: 1-[2-(5-methoxy-2-methyl-1H-indol-3-yl)ethyl]imidodicarbonimide diamide, trifluoroacetic acid salt

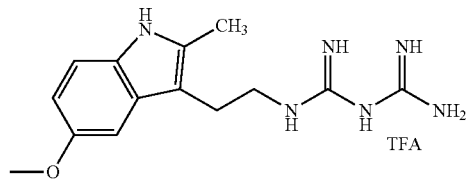 [SMILES: COc1ccc2[nH]c(C)c(CCNC(=N)NC(=N)N)c2c1]

Commercially available 2-(5-nmethoxy-2-methyl-1H-indol-3-yl)ethan-1-amine HCl (480 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 85 mg (11%) of 1-[2-(5-methoxy-2-methyl-1H-indol-3-yl)ethyl]imidodicarbonimide diamide, trifluoroacetic acid salt as an off-white solid. $^1$H NMR (600 MHz, DMSO-d$_6$) δ ppm 2.30 (s, 3H), 2.71-2.98 (m, 4H), 3.76 (s, 3H), 6.59 (m, 1H), 6.73-7.28 (m, 6H), 7.89 (s, br, 1H), 10.63 (m, 1H); LCMS calculated for C$_{14}$H$_{20}$N$_6$O: m/z=288; found: m/z=289 (M+H).

Example 20: 1-(2-(1H-pyrrolo[2,3-b]pyridin-3-yl)ethyl)imidodicarbonimide diamide hydrochloride

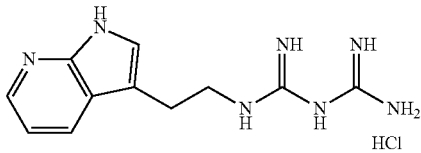 [SMILES: N=C(N)NC(=N)NCCc1c[nH]c2ncccc12 ; Cl]

Commercially available 2-(1H-pyrrolo[2,3-b]pyridin-3-yl)ethan-1-amine hydrochloride (395 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The crude material was triturated with 30 mL of isopropanol, filtered, then triturated with another 30 mL of isopropanol, filtered, and dried to give 1-(2-(1H-pyrrolo[2,3-b]pyridin-3-yl)ethyl)imidodicarbonimide diamide hydrochloride (140 mgs, 25% yield) as a tan solid. $^1$H NMR (600 MHz, DMSO-d$_6$) δ 2.86 (m, 2H), 3.38 (m, 1H), 3.56 (t, J=6.2, 1H), 6.47-6.92 (m, 4H), 6.99 (m, 4H), 7.16-7.40 (m, 2H), 7.93 (m, 1H), 8.16 (m, 1H); LCMS calculated for C$_{11}$H$_{15}$N$_7$: m/z=245; found: m/z=246 (M+H).

Example 21: 1-(2-(1H-pyrrolo[3,2-b]pyridin-3-yl)ethyl)imidodicarbonimide diamide acetate

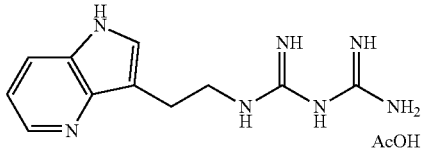 [SMILES: "AcOH" ; N=C(N)NC(=N)NCCc1c[nH]c2cccnc12]

Commercially available 2-(1H-pyrrolo[3,2-b]pyridin-3-yl)ethan-1-amine (200 mg; 1.24 mmol) was suspended in 10 ml of water and was treated with conc. HCl (12M; 225 μL; 2.7 mmol) to give a clear brown solution which was freeze-dried to afford a brown solid. The freeze-dried solid was pulverized under nitrogen atmosphere and mixed with cyanoguanidine (104 mg; 1.24 mmol) until homogeneous. The mixture was placed in a pre-heated mantle at 150° C. and heated for 48 min. The resulting brown "glass" was dissolved in methanol, concentrated in vacuo, and induced to foam to provide an amorphous brown solid/resin. The crude product was purified by reverse phase column chromatography (ISCO Combiflash R$_f$; 13 g C18 "Gold" column, eluted with 2-30% methanol/0.1 M aq. NH$_4$CO$_3$). Pure fractions were combined based on LCMS and freeze-dried to give a flocculent white solid. This product was taken up in water and treated with 2 eq. of acetic acid. The resulting solution was freeze-dried to give 32 mg (36% yield) of 1-(2-(1H-pyrrolo[3,2-b]pyridin-3-yl)ethyl)imidodicarbonimide diamide acetate as a white amorphous solid. $^1$H NMR (500 MHz, DMSO-d$_6$+D$_2$O): δ 1.73 (s, br, acetate ion), 2.95 (t, J=7.1, 2H), 3.41 (t, J=7.1, 2H), 7.11 (dd, J=4.5, 8.2, 1H), 7.48 (s, 1H), 7.75 (d, J=8.2, 1H), 8.27 (dd, J=1.5, 4.5, 1H); LCMS calculated for C$_{11}$H$_{15}$N$_7$: m/z=245; found: m/z=246 (M+H).

Example 22: 1-(2-(1H-pyrrolo[3,2-c]pyridin-3-yl)ethyl)imidodicarbonimide diamide hydrochloride

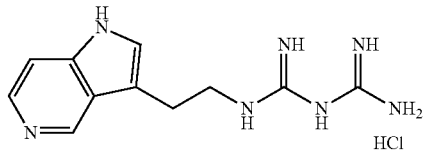 [SMILES: N=C(N)NC(=N)NCCc1c[nH]c2ccncc12 ; Cl]

Step 1: N,N-dimethyl-1-(1H-pyrrolo[3,2-c]pyridin-3-yl)methanamine 1H-pyrrolo[3,2-c]pyridine (302 mg; 2.56 mmol) in 5 mL of n-butanol was treated with dimethylamine hydrochloride (230 mg; 2.82 mmol) followed by paraformaldehyde (87 mg; 2.90 mmol formaldehyde). The mixture was stirred and heated at 120° C. for 3 hr then allowed to cool to room temperature overnight. The resulting mixture was filtered, and the residue was washed with EtOH. The combined filtrates were concentrated in vacuo to give a viscous amber liquid that was partitioned between 1.0 M NaOH and DCM. The aqueous phase was further extracted 6 times with DCM. The combined organic extracts were dried (MgSO$_4$), filtered, and concentrated in vacuo to give the crude product as a clear nearly colorless resin. The crude product was purified by silica gel column chromatography (ISCO Combiflash R$_f$, eluted with 0-30% methanol (1% aq. NH$_4$OH)/DCM) to give 267 mg (60% yield) of N,N-dimethyl-1-(1H-pyrrolo[3,2-c]pyridin-3-yl)methanamine as a clear colorless resin. $^1$H NMR (500 MHz, CDCl$_3$): δ 2.32 (s, 6H), 3.70 (s, 2H), 7.19 (s, 1H), 7.28 (d, J=6.1, 1H), 8.31 (d, J=6.1, 1H), 8.77 (s, br, 1H), 9.04 (s, 1H); LCMS calculated for C$_{10}$H$_{13}$N$_3$: m/z=175; found: m/z=176 (M+H).

Step 2: 2-(1H-pyrrolo[3,2-c]pyridin-3-yl)acetonitrile

N,N-dimethyl-1-(1H-pyrrolo[3,2-c]pyridin-3-yl)methanamine (260 mg; 1.48 mmol) in 3 mL of THF and 1.5 mL of EtOH (absolute) was treated with iodomethane (280 µL; 638 mg; 4.49 mmol). The solution slowly developed a precipitate and was stirred at rt for 18 hr. The resulting suspension was diluted with Et$_2$O, allowed to stir for 1 hr, and filtered. The residue was washed twice with Et$_2$O then dried in vacuo to give 440 mg of N,N,N-trimethyl-1-(1H-pyrrolo[3,2-c]pyridin-3-yl)methanaminium iodide as a beige powder. This material was dissolved in 5 mL of DMF and treated with sodium cyanide (140 mg; 2.86 mmol) in 4 mL of H$_2$O. The resulting solution was heated at 75° C. for 3 hr. The solution was cooled to rt and extracted with 20% methanol/DCM (8×20 mL). The combined extracts were dried (MgSO$_4$), filtered, and concentrated in vacuo. The resulting amber oil was repeatedly concentrated from ethyl acetate to remove entrained DMF and then was purified by silica gel column chromatography (ISCO Combiflash Rr, eluted with 1-20% methanol (1% aq. NH$_4$OH)/DCM) to give 60 mg (28% yield) of 2-(1H-pyrrolo[3,2-c]pyridin-3-yl)acetonitrile as a clear colorless resin which crystallized on standing. $^1$H NMR (500 MHz, CDCl$_3$): δ 3.92 (d, J=1.2, 2H), 7.31 (s, 1H), 7.33 (dd, J=1.2, 6.0, 1H), 8.40 (d, J=5.5, 1H), 8.58 (s, br, 1H), 8.95 (s, 1H); LCMS calculated for C$_9$H$_7$N$_3$: m/z=157; found: m/z=158 (M+H).

Step 3: 2-(1H-pyrrolo[3,2-c]pyridin-3-yl)ethan-1-amine hydrochloride 2-(1H-pyrrolo[3,2-c]pyridin-3-yl)acetonitrile (52 mg; 0.33 mmol) in 5 mL of dry THF was cooled to 0° C. under nitrogen atmosphere and treated with borane-THF (1.0M in THF; 1.35 mL). The resulting solution was stirred at 0° C. for 20 minutes then at rt for 14 hr. The reaction was again cooled to 0° C. and treated with additional borane-THF (1.30 mL) then allowed to stir at rt for an additional 24 hr. The reaction was cooled to 0° C., quenched by slow addition of methanol, allowed to come to rt, and concentrated in vacuo. The residue was taken up in MeOH and treated with 0.25 mL of conc. HCl to give a clear colorless solution which was stirred at room temperature for 1 hr. The solution was then conc. to remove the MeOH and freeze-dried. The off-white amorphous solid obtained from freeze-drying was dissolved in 2 mL of water and filtered through a 0.2 µm filter. The clear filtrate was again freeze-dried to give 58 mg (89% yield) of 2-(1H-pyrrolo[3,2-c]pyridin-3-yl)ethan-1-amine hydrochloride as an amorphous off-white solid. $^1$H NMR (500 MHz, CDCl$_3$): δ 3.38 (m, 2H), 7.83 (d, J=2.1, 1H), 7.93 (d, J=6.5, 1H), 8.01 (s, br, 3H), 8.40 (d, J=6.2, 1H), 9.39 (s, 1H); LCMS calculated for C$_9$H$_{11}$N$_3$: m/z=161; found: m/z=162 (M+H).

Step 4: 1-(2-(1H-pyrrolo[3,2-c]pyridin-3-yl)ethyl)imidodicarbonimide diamide hydrochloride 2-(1H-pyrrolo[3,2-c]pyridin-3-yl)ethan-1-amine hydrochloride (56 mg; 0.28 mmol) and cyanoguanidine (24 mg; 0.28 mmol) were thoroughly blended with a spatula. The mixture was then heated to 200° C. in a preheated mantle for 15 min and then cooled to rt. LCMS analysis of the fused material showed considerable conversion to product along with remaining SM. The mixture was again heated to 200° C. for 10 min then cooled to rt. The resulting amorphous solid was stirred and sonicated in 1,4-dioxane to obtain a finely divided homogeneous suspension. Solids were isolated and washed with 1,4-dioxane then dried under a stream of N2 to give a powder. The crude product was then stirred in 15 mL of refluxing 1,4-dioxane for 30 min. The mixture was allowed to cool and the supernatant was separated and conc. in vacuo to give a beige powder. This solid was stirred in refluxing EtOH to give a fine suspension. The hot supernatant was separated via filtration and diluted dropwise with 1,4-dioxane until a haze developed. Some precipitate developed and was separated. The supernatant was further diluted with 1,4-dioxane to induce a precipitate which formed a gummy solid. The solids were isolated, dried in vacuo, and induced to foam to give 33 mg (42% yield) of 1-(2-(1H-pyrrolo[3,2-c]pyridin-3-yl)ethyl)imidodicarbonimide diamide hydrochloride as a light amber amorphous solid. $^1$H NMR (500 MHz, DMSO-d$_6$): δ 3.01 (t, J=7.0, 2H), 3.43 (t, J=7.0, 2H), 6.80 (m, br, 6H), 7.68 (s, 1H), 7.81 (d, J=6.5, 1H), 8.34 (d, J=6.5, 1H), 9.20 (s, 1H), 12.39 (s, br, 1H); LCMS calculated for C$_{11}$H$_{15}$N$_7$: m/z=245; found: m/z=246 (M+H).

Example 23: 3-(2-(6-fluoro-1H-indol-3-yl)ethyl)-1,1-dimethyl imidodicarbonimide diamide hydrochloride

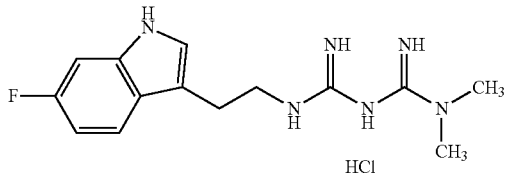 [SMILES: CN(C)C(=N)NC(=N)NCCc1c[nH]c2cc(F)ccc12 ; Cl]

Step 1: N,N-dimethyl dicyandiamide

Sodium dicyanamide (1 g, 11.2 mmol) and dimethyl amine (5.6 mL, 2M in THF, 11.2 mmol) were added to isopropanol (9 mL) in a sealed tube under $N_2$. Concentrated HCl (971 μL, 11.2 mmol) was added to the vessel. The sealed tube was placed in an oil bath and heated to 80° C. for 18 hr. After cooling to rt, the resulting solid material was filtered and rinsed with isopropanol. The filtrate was concentrated and dried under vacuum to obtain N,N-dimethyl dicyandiamide as a fluffy white solid.

Step 2: 3-(2-(6-fluoro-1H-indol-3-yl)ethyl)-1,1-dimethyl imidodicarbonimide diamide hydrochloride Commercially available 2-(6-fluoro-1H-indol-3-yl)ethan-1-amine HCl (428 mg, 2 mmol) and N,N-dimethyl dicyandiamide (244 mg, 2.4 mmol) were combined in a dry pear shaped flask under nitrogen. The flask was placed in a 160° C. oil bath and stirred for 3-4 hr until LC/MS analysis showed that the desired biguanide was the major product of the mixture. After cooling to rt, 30 mL of a hot methanol/isopropanol mixture (1:2) was added and the resulting solid removed by filtration. The filtrate was concentrated and triturated with isopropanol. The resulting solid was isolated by filtration and dried under vacuum to give 3-(2-(6-fluoro-1H-indol-3-yl)ethyl)-1,1-dimethyl imidodicarbonimide diamide hydrochloride (300 mg, 46% yield) as a white solid. $^1$H NMR (600 MHz, DMSO-$d_6$) δ ppm 2.83 (t, J=7.0, 2H), 2.89 (s, 6H), 3.34 (t, J=5.9, 2H), 6.56 (s, br, 2H), 6.81 (m, 1H), 6.95-7.25 (m, 4H), 7.40-7.54 (m, 1H), 10.89 (s, br, 1H); LCMS calculated for $C_{14}H_{19}FN_6$: m/z=290; found: m/z=291 (M+H).

Example 24: 3-(2-(5-fluoro-1H-indol-3-yl)ethyl)-1,1-dimethyl imidodicarbonimide diamide hydrochloride

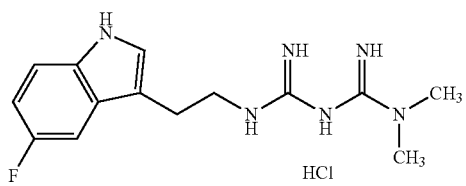 [SMILES: CN(C)C(=N)NC(=N)NCCc1c[nH]c2ccc(F)cc12 ; Cl]

Commercially available 2-(5-fluoro-1H-indol-3-yl)ethan-1-amine HCl (428 mg, 2 mmol) and N,N-dimethyl dicyandiamide (see Example 23 for preparation) (244 mg, 2.4 mmol) were combined in a dry pear shaped flask under nitrogen. The flask was placed in a 160° C. oil bath and stirred for 3-4 hr until LC/MS analysis showed that the desired biguanide was the major product of the mixture. After cooling to rt, 30 mL of a hot methanol/isopropanol mixture (1:2) was added and the resulting solid removed by filtration. The filtrate was concentrated and triturated with isopropanol. The resulting solid was isolated by filtration and dried under vacuum to give 3-(2-(5-fluoro-1H-indol-3-yl)ethyl)-1,1-dimethyl imidodicarbonimide diamide hydrochloride (160 mg, 25% yield) as a white solid. $^1$H NMR (600 MHz, DMSO-$d_6$) δ ppm 2.79 (m, 2H), 2.90 (s, 6H), 3.34 (m, 2H), 6.59 (s, br, 2H), 6.86 (s, br, 1H), 7.09 (m, 3H), 7.24 (m, 2H), 7.29 (dd, J=4.5, 8.6, 1H), 10.93 (s, br, 1H); LCMS calculated for $C_{14}H_{19}FN_6$: m/z=290; found: m/z=291 (M+H).

Example 25: 1-[2-(5-trifluoromethyl-1H-indol-3-yl)ethyl]imidodicarbonimide diamide, trifluoroacetic acid salt

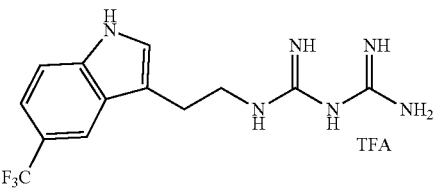 [SMILES: N=C(N)NC(=N)NCCc1c[nH]c2ccc(C(F)(F)F)cc12]

Commercially available 2-(5-trifluoromethyl-1H-indol-3-yl)ethan-1-amine HCl (528 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—$H_2O$ (2-3 mL), and purified by reverse phase semi-preparative HPLC eluting with gradient of $H_2O$-MeOH (Mobile Phase A: $H_2O$ (0.05% TFA); Mobile Phase B: MeOH (0.05% TFA)) for 30 minutes. Mobile Phase B is 0% at the start and reaches 100% at 20 minutes and maintained until t=30 minutes) to afford 45 mg (5%) of 1-[2-(5-trifluoromethyl-1H-indol-3-yl)ethyl] imidodicarbonimide diamide, trifluoroacetic acid salt as a white solid. $^1$H NMR (600 MHz, DMSO-$d_6$) δ 2.96 (t, J=7.0, 2H), 3.39 (m, 2H), 6.86 (s, br, 3H) 7.27-7.65 (m, 6H) 7.95 (s, 1H) 11.40 (s, br 1H); LCMS calculated for $C_{13}H_{15}F_3N_6$: m/z=312; found: m/z=313 (M+H).

Example 26: 1-[2-(4-fluoro-1H-indol-3-yl)ethyl]imidodicarbonimide diamide, trifluoroacetic acid salt

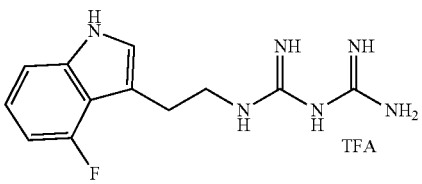 [SMILES: N=C(N)NC(=N)NCCc1c[nH]c2cccc(F)c12]

Commercially available 2-(4-fluoro-1H-indol-3-yl)ethan-1-amine HCl (428 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 38 mg (5%) of 1-[2-(4-fluoro-1H-indol-3-yl)ethyl]imidodicarbonimide diamide, trifluoroacetic acid salt as a white solid. $^1$H NMR (600 MHz, DMSO-d$_6$) δ 2.98 (t, J=7.0, 2H), 3.39 (m, 2H), 6.73 (dd, J=8.2, 11.1, 1H), 6.81-7.11 (m, 4H), 7.12-7.47 (m, 4H), 7.55 (s, br, 1H), 11.23 (s, br, 1H); LCMS calculated for C$_{12}$H$_{15}$FN$_6$: m/z=262; found: m/z=263 (M+H).

Example 27: 1-[2-(5,7-difluoro-1H-indol-3-yl)ethyl]imidodicarbonimide diamide, trifluoroacetic acid salt

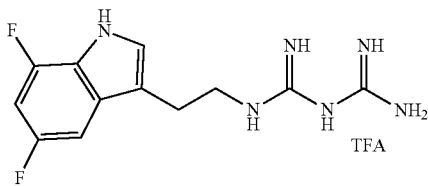 [SMILES: N=C(N)NC(=N)NCCc1c[nH]c2c(F)cc(F)cc12]

Commercially available 2-(5,7-difluoro-1H-indol-3-yl)ethan-1-amine HCl (452 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 43 mg (5%) of 1-[2-(5,7-difluoro-1H-indol-3-yl)ethyl]imidodicarbonimide diamide, trifluoroacetic acid salt as a white solid. $^1$H NMR (600 MHz, DMSO-d$_6$) δ 2.87 (t, J=7.2, 2H), 3.22-3.38 (m, 2H, overlapped with H$_2$O peak), 6.96 (m, 4H), 7.13-7.54 (m, 5H), 11.54 (s, br, 1H); LCMS calculated for C$_{12}$H$_{14}$F$_2$N$_6$: m/z=280; found: m/z=281 (M+H).

Example 28: 1-[2-(5,6-difluoro-1H-indol-3-yl)ethyl]imidodicarbonimide diamide, trifluoroacetic acid salt

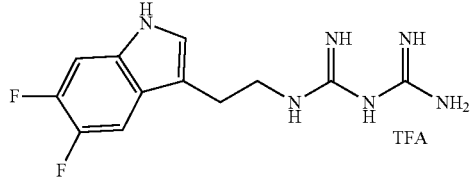 [SMILES: N=C(N)NC(=N)NCCc1c[nH]c2cc(F)c(F)cc12]

Commercially available 2-(5,6-difluoro-1H-indol-3-yl)ethan-1-amine HCl (452 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 10 mg (2%) of 1-[2-(5,6-difluoro-1H-indol-3-yl)ethyl]imidodicarbonimide diamide, trifluoroacetic acid salt as a brown solid. $^1$H NMR (600 MHz, DMSO-d$_6$) δ 2.86 (t, J=7.2, 2H), 3.38 (m, 2H), 6.65-7.47 (m, 7H), 7.54 (s, br, 1H), 7.85 (s, br, 1H), 11.08 (s, br, 1H); LCMS calculated for C$_{12}$H$_{14}$F$_2$N$_6$: m/z=280; found: m/z=281 (M+H).

Example 29: 1-[2-(5-fluoro-2-methyl-1H-indol-3-yl)ethyl]imidodicarbonimide diamide, trifluoroacetic acid salt

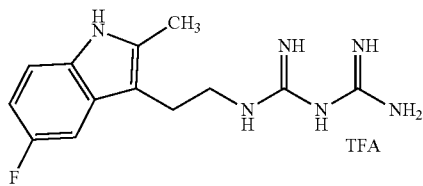 [SMILES: Cc1[nH]c2ccc(F)cc2c1CCNC(=N)NC(=N)N]

Commercially available 2-(5-fluoro-2-methyl-1H-indol-3-yl)ethan-1-amine HCl (456 mg, 2 mmol) and dicyandiamide (168 mg, 2 mmol) were combined in a dry pear shaped flask under nitrogen. The contents were heated to 170° C. under stirring, with the materials forming a melt once the bath temperature was between 160-170° C. The resulting melt was heated for 3 hr then allowed to cool to rt. The contents were treated with hot MeOH-isopropanol mixture (30 mL, 1:2) and then filtered. The filtrate was concentrated, and the residue was dissolved in 1:1 MeOH—H$_2$O (2-3 mL), and purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and maintained until t=30 minutes) to afford 42 mg (6%) of 1-[2-(5-fluoro-2- methyl-1H-indol-3-yl)ethyl]imidodicarbonimide diamide, trifluoroacetic acid salt as a tan solid. ¹H NMR (600 MHz, DMSO-d₆) δ 2.33 (s, 3H), 2.82 (m, 2H), 3.28 (m, 2H), 6.81 (s, br, 2H), 6.88-7.33 (m, 5H), 7.34-8.45 (m, 2H), 10.92 (s, br, 1H); LCMS calculated for $C_{13}H_{17}FN_6$: m/z=276; found: m/z=277 (M+H).

Example 30: 1-(2-(1H-pyrrolo[2,3-b]pyridin-3-yl) ethyl)-1,1-dimethyl imidodicarbonimide diamide trifluoroacetic acid salt

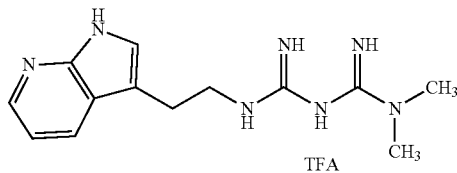 [SMILES: CN(C)C(=N)NC(=N)NCCc1c[nH]c2ncccc12]

Commercially available 2-(1H-pyrrolo[2,3-b]pyridin-3-yl)ethan-1-amine HCl (394 mg, 2 mmol) and N,N-dimethyl dicyandiamide (244 mg, 2.4 mmol) were combined in a dry pear shaped flask under nitrogen. The flask was placed in a 160° C. oil bath and stirred for 3-4 hr until LC/MS analysis showed that the desired biguanide was the major product of the mixture. After cooling to rt, 30 mL of a hot methanol/isopropanol mixture (1:2) was added and the resulting solid removed by filtration. The filtrate was concentrated and triturated with isopropanol. The resulting solid was isolated and further purified by reverse phase semi-preparative HPLC eluting with gradient of H₂O-MeOH (Mobile Phase A: H₂O (0.05% TFA); Mobile Phase B: MeOH (0.05% TFA)) for 30 minutes. Mobile Phase B is 0% at the start and reaches 100% at 20 minutes and maintained until t=30 minutes) to afford 55 mg (7% yield) of 1-(2-(1H-pyrrolo[2,3-b]pyridin-3-yl)ethyl)-1,1-dimethyl imidodicarbonimide diamide trifluoroacetic acid salt as a tan solid. ¹H NMR (600 MHz, DMSO-d₆) δ 2.84-2.97 (m, 8H), 3.41 (m, 2H), 6.50 (s, br, 1H), 6.91-7.51 (m, 5H), 8.04 (d, J=7.6, 1H), 8.23 (d, J=3.5, 1H), 11.58 (s, br, 1H); LCMS calculated for $C_{13}H_{19}N_7$: m/z=273; found: m/z=274 (M+H).

Example 31: 1-[2-(6-fluoro-2-methyl-1H-indol-3-yl) ethyl]imidodicarbonimide diamide, trifluoroacetic acid salt

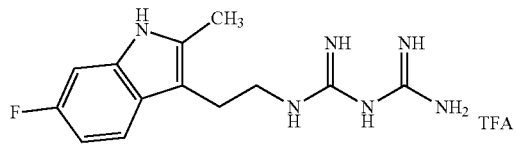 [SMILES: Cc1[nH]c2cc(F)ccc2c1CCNC(=N)NC(=N)N]

Commercially available 2-(6-fluoro-2-methyl-1H-indol-3-yl)ethan-1-amine HCl (457 mg, 2 mmol) and dicyandiamide (168 mg, 2 mmol) were combined in a dry pear shaped flask under nitrogen. The contents were heated to 170° C. under stirring, with the materials forming a melt once the bath temperature was between 165-170° C. The resulting melt was heated for 3 hr and then allowed to cool to room temperature. The contents were treated with hot MeOH-IPA mixture (30 mL, 1:2) and then filtered. The filtrate was concentrated and the residue was dissolved in 1:1 MeOH—H₂O (2-3 mL) and half of the material was purified by reverse phase semi-preparative HPLC eluting with gradient of H₂O-MeOH (Mobile Phase A: H₂O (0.05% TFA); Mobile Phase B: MeOH (0.05% TFA)) for 30 minutes. Mobile Phase B is 0% at the start and reaches 100% at 20 minutes and is maintained there until t=30 minutes to afford 80 mg of 1-[2-(6-fluoro-2-methyl-1H-indol-3-yl) ethyl]imidodicarbonimide diamide, trifluoroacetic acid salt as a gummy solid. ¹H NMR (600 MHz, DMSO-d₆) δ 2.25-2.32 (m, 3H), 2.76 (br,s, 2H), 3.21 (br, s, 2H), 6.52-7.10 (m, 7H), 7.17 (dd, J=8.49, 4.10 Hz, 2H), 10.85 (br,s, 1H); LCMS ESI calculated for $C_{13}H_{17}FN_6$: m/z=276; found: m/z=277 (M+H).

Example 32: 3-(2-(5-trifluoromethyl-1H-indol-3-yl) ethyl)-1,1-dimethyl imidodicarbonimide diamide hydrochloride

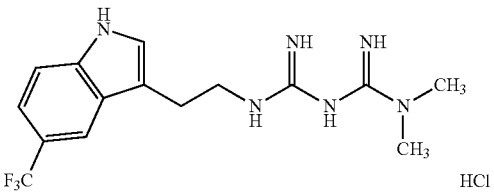 [SMILES: CN(C)C(=N)NC(=N)NCCc1c[nH]c2ccc(C(F)(F)F)cc12 ; Cl]

Commercially available 2-(5-trifluoromethyl-1H-indol-3-yl)ethan-1-amine HCl (529 mg, 2 mmol) and N,N-dimethyl dicyandiamide (see Example 23 for preparation) (244 mg, 2.4 mmol) were combined in a dry pear shaped flask under nitrogen. The contents were heated to 170° C. under stirring, with the materials forming a melt once the bath temperature was between 165-170° C. The resulting melt was heated for 3 hr then allowed to cool to room temperature. The contents were treated with hot MeOH-IPA mixture (30 mL, 1:2) and then filtered. This material was triturated with IPA to yield 3-(2-(5-trifluoromethyl-1H-indol-3-yl)ethyl)-1,1-dimethyl imidodicarbonimide diamide HCl (120 mg) as a white solid. ¹H NMR (600 MHz, DMSO-d₆) δ 2.89 (s, 6H), 2.89-2.93 (m, 2H), 3.31-3.39 (m, 2H), 6.19-7.27 (m, 6H), 7.30-7.37 (m, 2H), 7.50 (d, J=8.49 Hz, 1H), 7.89 (s, 1H), 11.32 (br, s, 1H); LCMS ESI calculated for $C_{15}H_{19}F_3N_6$: m/z=340; found: m/z=341 (M+H).

Example 33: 3-(2-(5-trifluoromethoxy-1H-indol-3-yl)ethyl)-1,1-dimethyl imidodicarbonimide diamide hydrochloride

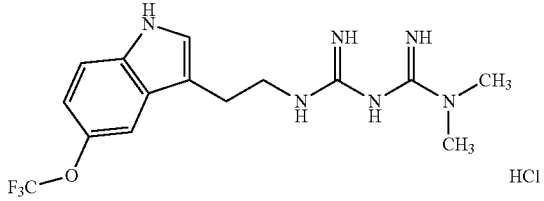 [SMILES: CN(C)C(=N)NC(=N)NCCc1c[nH]c2ccc(OC(F)(F)F)cc12 ; Cl]

Commercially available 2-(5-trifluoromethoxy-1H-indol-3-yl)ethan-1-amine HCl (561 mg, 2 mmol) and N,N-dimethyl dicyandiamide (see Example 23 for preparation) (244 mg, 2.4 mmol) were combined in a dry pear shaped flask under nitrogen. The contents were heated to 170° C. under stirring, with the materials forming a melt once the bath temperature was between 165-170° C. The resulting melt was heated for 3 hr then allowed to cool to room temperature. The contents were treated with hot MeOH-IPA mixture (30 mL, 1:2) and then filtered. This material was triturated with IPA to yield 3-(2-(5-trifluoromethoxy-1H-indol-3-yl)ethyl)-1,1-dimethyl imidodicarbonimide diamide hydrochloride (120 mg) as a tan solid. $^1$H NMR (600 MHz, DMSO-$d_6$) δ 2.81-2.87 (m, 2H), 2.89 (s, 6H), 3.31-3.36 (m, 2H), 6.30-7.28 (m, 7H), 7.30 (s, 1H), 7.39 (d, J=8.8 Hz, 1H), 7.47 (s, 1H), 11.16 (s, br, 1H); LCMS ESI calculated for $C_{15}H_{19}F_3N_6O$: m/z=356; found: m/z=357 (M+H).

Example 34: 1-[2-(4-chloro-1H-indol-3-yl)ethyl]imidodicarbonimide diamide, trifluoroacetic acid salt

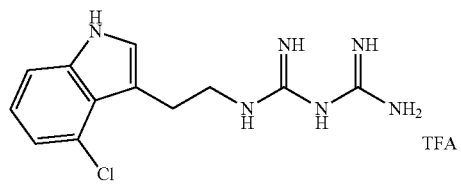 [SMILES: N=C(N)NC(=N)NCCc1c[nH]c2cccc(Cl)c12]

Commercially available 2-(4-chloro-1H-indol-3-yl)ethan-1-amine HCl (462 mg, 2 mmol) and dicyandiamide (168 mg, 2 mmol) were combined in a dry pear shaped flask under nitrogen. The contents were heated to 170° C. under stirring, with the materials forming a melt once the bath temperature was between 165-170° C. The resulting melt was heated for 3 hr and then allowed to cool to room temperature. The contents were treated with hot MeOH-IPA mixture (30 mL, 1:2) and then filtered. The filtrate was concentrated and the residue was dissolved in 1:1 MeOH—H$_2$O (2-3 mL) and half of the material was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 45 mg of 1-[2-(4-chloro-1H-indol-3-yl)ethyl]imidodicarbonimide diamide, trifluoroacetic acid salt as a gummy solid. $^1$H NMR (600 MHz, DMSO-$d_6$) δ 3.06-3.13 (m, 2H), 3.37-3.42 (m, 2H), 6.78-7.12 (m, 8H), 7.26 (s, 1H), 7.31 (d, J=7.83 Hz, 1H), 11.25 (s, 1H); LCMS ESI calculated for $C_{12}H_{15}ClN_6$: m/z=278; found: m/z=279 (M+H).

Example 35: 1-[2-(6-chloro-1H-indol-3-yl)ethyl]imidodicarbonimide diamide, trifluoroacetic acid salt

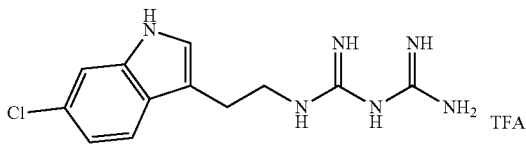 [SMILES: N=C(N)NC(=N)NCCc1c[nH]c2cc(Cl)ccc12]

Commercially available 2-(6-chloro-1H-indol-3-yl)ethan-1-amine HCl (231 mg, 1 mmol) and commercially available 1-carbamimidoyl-2-methyl-isothiourea hydroiodide (264 mg, 2 mmol) were combined in a flask under nitrogen. Ethanol (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 45 mg of 1-[2-(6-chloro-1H-indol-3-yl)ethyl]imidodicarbonimide diamide trifluoroacetic acid salt as a gummy solid. $^1$H NMR (600 MHz, DMSO-$d_6$) δ 2.83 (s, br, 2H), 3.45-3.50 (m, 2H), 6.86 (s, br, 6H), 6.96 (dd, J=8.5, 1.5 Hz, 1H), 7.18 (s, 1H), 7.35 (d, J=1.76 Hz, 1H), 7.51 (d, J=8.5 Hz, 1H), 10.98 (s, br, 1H); LCMS ESI calculated for $C_{12}H_{15}ClN_6$: m/z=278; found: m/z=279 (M+H).

Example 36: 1-[2-(7-chloro-1H-indol-3-yl)ethyl]imidodicarbonimide diamide, trifluoroacetic acid salt

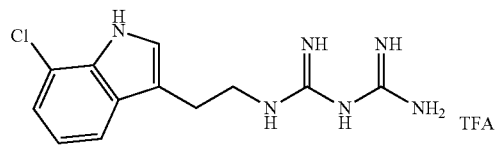 [SMILES: N=C(N)NC(=N)NCCc1c[nH]c2c(Cl)cccc12]

Commercially available 2-(7-chloro-1H-indol-3-yl)ethan-1-amine HCl (231 mg, 1 mmol) and commercially available 1-carbamimidoyl-2-methyl-isothiourea hydroiodide (264 mg, 2 mmol) were combined in a flask under nitrogen. Ethanol (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 10 mg of 1-[2-(7-chloro-1H-indol-3-yl)ethyl]imidodicarbonimide diamide trifluoroacetic acid salt as a gummy solid. $^1$H NMR (600 MHz, DMSO-$d_6$) δ 2.86 (s, br, 2H), 3.32-3.38 (m, 2H), 6.48-7.05 (m, 7H), 7.12 (d, J=7.3 Hz, 1H), 7.23 (s, 1H), 7.49 (d, J=7.9 Hz, 1H), 11.20 (s, br, 1H); LCMS ESI calculated for $C_{12}H_{15}ClN_6$: m/z=278; found: m/z=279 (M+H).

Example 37: 1-[2-(6-fluoro-5-methyl-1H-indol-3-yl)ethyl]imidodicarbonimide diamide, trifluoroacetic acid salt

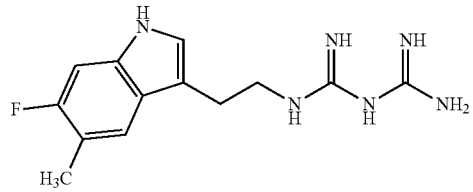

Commercially available 2-(6-fluoro-5-methyl-1H-indol-3-yl)ethan-1-amine HCl (229 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 30 mg of 1-[2-(6-fluoro-5-methyl-1H-indol-3-yl)ethyl]imidodicarbonimide diamide trifluoroacetic acid salt as a gummy solid. $^1$H NMR (600 MHz, DMSO-d$_6$) δ 2.47 (s, 3H), 3.02 (s, br, 2H), 3.55 (s, br, 2H), 7.11 (s, br, 6H), 7.20-7.38 (m, 2H), 7.56 (s, 1H), 10.97 (s, br, 1H); LCMS ESI calculated for C$_{13}$H$_{17}$FN$_6$: m/z=276; found: m/z=277 (M+H).

Example 38: 1-[2-(7-chloro-5-fluoro-1H-indol-3-yl)ethyl]imidodicarbonimide diamide, trifluoroacetic acid salt

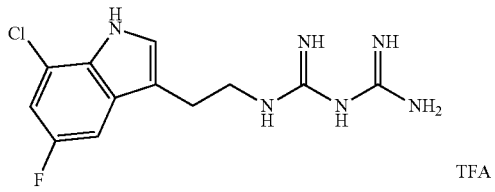 [SMILES: N=C(N)NC(=N)NCCc1c[nH]c2c(Cl)cc(F)cc12]

Commercially available 2-(7-chloro-5-fluoro-1H-indol-3-yl)ethan-1-amine HCl (249 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 30 mg of 1-[2-(7-chloro-5-fluoro-1H-indol-3-yl)ethyl]imidodicarbonimide diamide trifluoroacetic acid salt as a gummy solid. $^1$H NMR (600 MHz, DMSO-d$_6$) δ 2.84 (t, J=7.1 Hz, 2H) 3.24-3.32 (m, 2H), 6.81 (s, br, 6H), 7.14 (dd, J=9.3, 2.0 Hz, 1H), 7.27 7.40 (m, 2H), 11.35 (s, br, 1H); LCMS ESI calculated for C$_{12}$H$_{14}$ClFN$_6$: m/z=296; found: m/z=297 (M+H).

Example 39: 1-(2-(1-methyl-1H-pyrrolo[2,3-b]pyridin-3-yl)ethyl)imidodicarbonimide diamide, trifluoroacetic acid salt

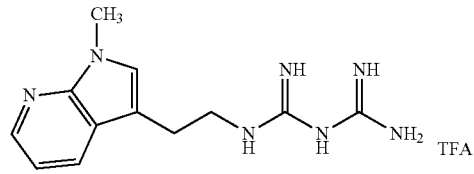 [SMILES: Cn1cc(CCNC(=N)NC(=N)N)c2cccnc21]

Commercially available 2-(1-methyl-1H-pyrrolo[2,3-b]pyridin-3-yl)ethan-1-amine HCl (212 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 45 mg of 1-(2-(1-methyl-1H-pyrrolo[2,3-b]pyridin-3-yl)ethyl)imidodicarbonimide diamide trifluoroacetic acid salt as a tan solid. $^1$H NMR (600 MHz, DMSO-d$_6$) δ 2.79-2.94 (m, 2H), 3.31-3.45 (m, 2H), 3.75-3.79 (s, 3H), 7.00 (s, br, 6H), 7.07 (dd, J=7.8, 4.4 Hz, 1H), 7.30-7.37 (m, 1H), 7.98 (d, J=6.4 Hz, 1H), 8.24 (d, J=2.9 Hz, 1H); LCMS ESI calculated for C$_{12}$H$_{17}$N$_7$: m/z=259; found: m/z=260 (M+H).

Example 40: 1-(2-(5-chloro-1H-pyrrolo[2,3-b]pyridin-3-yl)ethyl)imidodicarbonimide diamide, trifluoroacetic acid salt

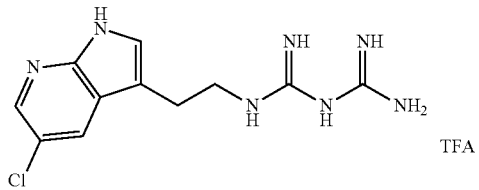 [SMILES: N=C(N)NC(=N)NCCc1c[nH]c2ncc(Cl)cc12]

Commercially available 2-(5-chloro-1H-pyrrolo[2,3-b]pyridin-3-yl)ethan-1-amine HCl (232 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 35 mg of 1-(2-(5-chloro-1H-pyrrolo[2,3-b]pyridin-3-yl)ethyl)imidodicarbonimide diamide trifluoroacetic acid salt as a yellow solid. $^1$H NMR (600 MHz, DMSO-d$_6$) δ 2.86 (s, br, 2H), 3.37 (ddd, J=13.1, 6.5, 6.4 Hz, 2H), 6.91 (d, J=1.2 Hz, 6H), 7.39 (s, br, 1H), 8.05-8.14 (m, 1H), 8.17 (d, J=2.5 Hz, 1H), 11.66 (s, br, 1H); LCMS ESI calculated for C$_{11}$H$_{14}$ClN$_7$: m/z=279; found: m/z=280 (M+H).

Example 41: 1-[2-(5,6,7-trifluoro-1H-indol-3-yl)ethyl]imidodicarbonimide diamide, trifluoroacetic acid salt

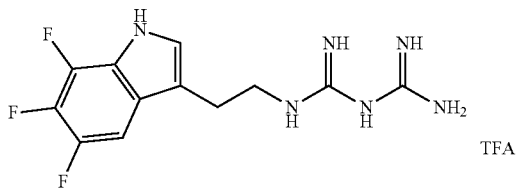 [SMILES: N=C(N)NC(=N)NCCc1c[nH]c2c(F)c(F)c(F)cc12]

Commercially available 2-(5,6,7-trifluoro-1H-indol-3-yl)ethan-1-amine HCl (251 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 25 mg of 1-[2-(5,6,7-trifluoro-1H-indol-3-yl)ethyl]imidodicarbonimide diamide trifluoroacetic acid salt as a viscous oil. $^1$H NMR (600 MHz, DMSO-d$_6$) δ 2.84 (t, J=7.1 Hz, 2H), 3.29-3.38 (m, 2H), 6.85 (s, br, 6H), 7.34 (d, J=2.0 Hz, 1H), 7.42 (dd, J=10.3, 6.4 Hz, 1H), 11.67 (s, 3H); LCMS ESI calculated for C$_{12}$H$_{13}$F$_3$N$_6$: m/z=298; found: m/z=299 (M+H).

Example 42: 1-[2-(4,5,6,7-tetrafluoro-1H-indol-3-yl)ethyl]imidodicarbonimide diamide, trifluoroacetic acid salt

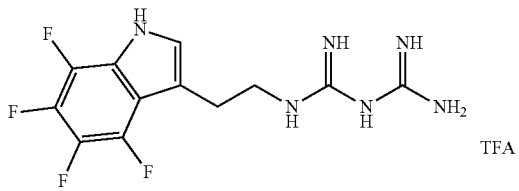 [SMILES: N=C(N)NC(=N)NCCc1c[nH]c2c(F)c(F)c(F)c(F)c12]

Commercially available 2-(4,5,6,7-tetrafluoro-1H-indol-3-yl)ethan-1-amine HCl (269 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 45 mg of 1-[2-(4,5,6,7-tetrafluoro-1H-indol-3-yl)ethyl]imidodicarbonimide diamide trifluoroacetic acid salt as a gummy solid. $^1$H NMR (600 MHz, DMSO-d$_6$) δ 2.93 (s, br, 2H), 3.16 (m, 2H), 6.80 (m, 6H), 7.37 (s, br, 1H), 12.01 (s, br, 1H); LCMS ESI calculated for C$_{12}$H$_{12}$F$_4$N$_6$: m/z=316; found: m/z=317 (M+H).

Example 43: 1-(2-(5-fluoro-1H-pyrrolo[2,3-b]pyridin-3-yl)ethyl)imidodicarbonimide diamide, trifluoroacetic acid salt

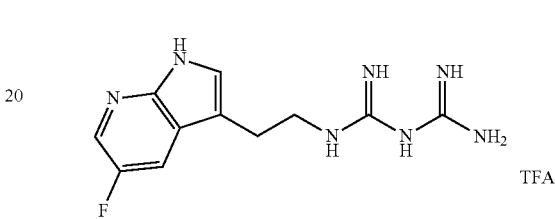

Commercially available 2-(5-fluoro-1H-pyrrolo[2,3-b]pyridin-3-yl)ethan-1-amine HCl (216 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 35 mg of 1-(2-(5-fluoro-1H-pyrrolo[2,3-b]pyridin-3-yl)ethyl)imidodicarbonimide diamide trifluoroacetic acid salt as a yellow solid. $^1$H NMR (600 MHz, DMSO-d$_6$) δ 2.85 (t, J=7.1 Hz, 2H), 3.30-3.43 (m, 2H), 6.93 (s, br, 6H), 7.40 (d, J=2.5 Hz, 1H), 7.84 (dd, J=9.8, 2.5 Hz, 1H), 8.16 (s, 1H), 11.56 (s, br, 1H); LCMS ESI calculated for C$_{11}$H$_{14}$FN$_7$: m/z=263; found: m/z=264 (M+H).

Example 44: 1-(2-(2-methyl-1H-pyrrolo[2,3-b]pyridin-3-yl)ethyl)imidodicarbonimide diamide, trifluoroacetic acid salt

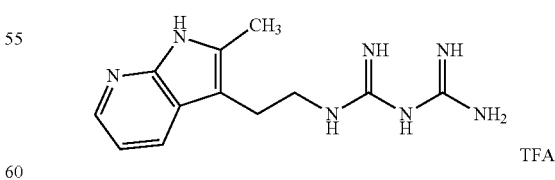

Commercially available 2-(2-methyl-1H-pyrrolo[2,3-b]pyridin-3-yl)ethan-1-amine HCl (212 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 35 mg of 1-(2-(2-methyl-1H-pyrrolo[2,3-b]pyridin-3-yl)ethyl)imidodicarbonimide diamide trifluoroacetic acid salt as a gummy solid. $^1$H NMR (600 MHz, DMSO-d$_6$) δ 2.35 (s, 3H), 2.79-2.89 (m, 2H), 3.22-3.33 (m, 2H), 6.44-7.40 (m, 7H), 7.99 (d, J=7.8 Hz, 1H), 8.14 (d, J=3.9 Hz, 1H), 11.64 (s, br, 1H); LCMS ESI calculated for C$_{12}$H$_{17}$N$_7$: m/z=259; found: m/z=260 (M+H).

Example 45: 1-(2-(6-fluoro-1H-pyrrolo[2,3-b]pyridin-3-yl)ethyl)imidodicarbonimide diamide, trifluoroacetic acid salt

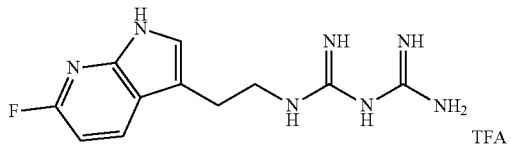 [SMILES: N=C(N)NC(=N)NCCc1c[nH]c2nc(F)ccc12]

Commercially available 2-(6-fluoro-1H-pyrrolo[2,3-b]pyridin-3-yl)ethan-1-amine HCl (216 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 60 mg of 1-(2-(6-fluoro-1H-pyrrolo[2,3-b]pyridin-3-yl)ethyl)imidodicarbonimide diamide trifluoroacetic acid salt as a light brown solid. $^1$H NMR (600 MHz, DMSO-d$_6$) δ 2.87 (t, J=7.1 Hz, 2H), 3.34-3.41 (m, 2H), 6.42-7.07 (m, 7H), 7.24 (d, J=2.0 Hz, 1H), 8.10 (t, J=8.3 Hz, 1H), 11.54 (s, br, 1H); LCMS ESI calculated for C$_{11}$H$_{14}$FN$_7$: m/z=263; found: m/z=264 (M+H).

Example 46: 1-(2-(4-chloro-1H-pyrrolo[2,3-b]pyridin-3-yl)ethyl)imidodicarbonimide diamide, trifluoroacetic acid salt

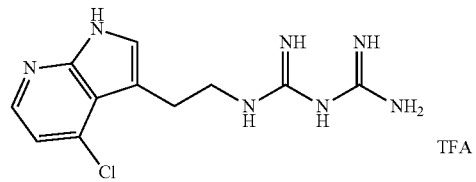 [SMILES: N=C(N)NC(=N)NCCc1c[nH]c2nccc(Cl)c12]

Commercially available 2-(4-chloro-1H-pyrrolo[2,3-b]pyridin-3-yl)ethan-1-amine HCl (232 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 80 mg of 1-(2-(4-chloro-1H-pyrrolo[2,3-b]pyridin-3-yl)ethyl)imidodicarbonimide diamide trifluoroacetic acid salt as a viscous oil. $^1$H NMR (600 MHz, DMSO-d$_6$) δ 3.02-3.12 (m, 2H), 3.36-3.47 (m, 2H), 6.90 (s, br, 6H), 7.08-7.15 (m, 1H), 7.40 (d, J=2.5 Hz, 1H), 8.08-8.14 (m, 1H), 11.83 (s, br, 1H); LCMS ESI calculated for C$_{11}$H$_{14}$ClN$_7$: m/z=279; found: m/z=280 (M+H).

Example 47: 1-[2-(4-chloro-5-fluoro-1H-indol-3-yl)ethyl]imidodicarbonimide diamide, trifluoroacetic acid salt

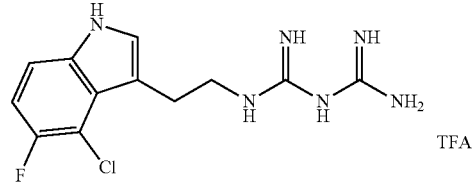 [SMILES: N=C(N)NC(=N)NCCc1c[nH]c2ccc(F)c(Cl)c12]

Commercially available 2-(4-chloro-5-fluoro-1H-indol-3-yl)ethan-1-amine HCl (249 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 40 mg of 1-[2-(4-chloro-5-fluoro-1H-indol-3-yl)ethyl]imidodicarbonimide diamide, trifluoroacetic acid salt as a gummy solid. $^1$H NMR (600 MHz, DMSO-d$_6$) δ ppm 3.04-3.14 (m, 2H), 3.35-3.45 (m, 2H), 6.92 (s, br, 6H), 7.03-7.12 (m, 1H), 7.25-7.39 (m, 2H), 11.32 (s, br, 1H); LCMS ESI calculated for C$_{12}$H$_{14}$ClFN$_6$: m/z=296; found: m/z=297 (M+H).

Example 48: 1-[2-(6-chloro-5-fluoro-1H-indol-3-yl)ethyl]imidodicarbonimide diamide, trifluoroacetic acid salt

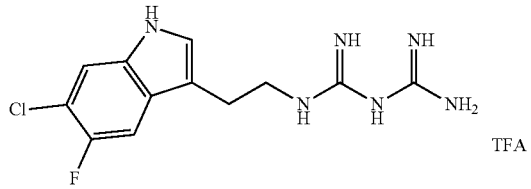 [SMILES: N=C(N)NC(=N)NCCc1c[nH]c2cc(Cl)c(F)cc12]

Commercially available 2-(6-chloro-5-fluoro-1H-indol-3-yl)ethan-1-amine HCl (249 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 45 mg of 1-[2-(6-chloro-5-fluoro-1H-indol-3-yl)ethyl]imidodicarbonimide diamide, trifluoroacetic acid salt as a gummy solid. $^1$H NMR (600 MHz, DMSO-d$_6$) δ ppm 2.78-2.90 (m, 2H), 3.29-3.36 (m, 2H), 6.86 (s, br, 6H), 7.29 (d, J=2.5 Hz, 1H), 7.45-7.55 (m, 2H), 11.07 (s, br, 1H); LCMS ESI calculated for C$_{12}$H$_{14}$ClFN$_6$: m/z=296; found: m/z=297 (M+H).

Example 49: 1-[2-(5-chloro-4-fluoro-1H-indol-3-yl)ethyl]imidodicarbonimide diamide, trifluoroacetic acid salt

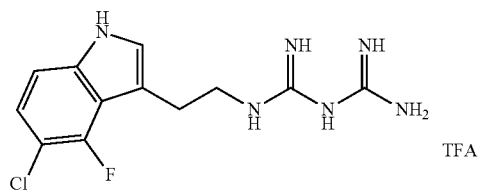 [SMILES: N=C(N)NC(=N)NCCc1c[nH]c2ccc(Cl)c(F)c12]

Commercially available 2-(5-chloro-4-fluoro-1H-indol-3-yl)ethan-1-amine HCl (249 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 40 mg of 1-[2-(5-chloro-4-fluoro-1H-indol-3-yl)ethyl]imidodicarbonimide diamide, trifluoroacetic acid salt as a tan solid. $^1$H NMR (600 MHz, DMSO-d$_6$) ppm 2.95 (s, br, 2H), 3.31-3.46 (m, 2H), 6.88 (s, br, 6H), 7.06-7.16 (m, 1H), 7.20 (d, J=7.8 Hz, 1H), 7.26 (s, 1H), 11.35 (s, br, 1H); LCMS ESI calculated for C$_{12}$H$_{14}$ClFN$_6$: m/z=296; found: m/z=297 (M+H).

Example 50: 1-[2-(4,5,6-trifluoro-1H-indol-3-yl)ethyl]imidodicarbonimide diamide, trifluoroacetic acid salt

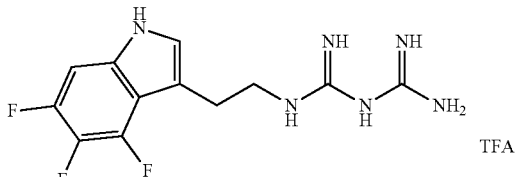

Commercially available 2-(4,5,6-trifluoro-1H-indol-3-yl)ethan-1-amine HCl (251 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 42 mg of 1-[2-(4,5,6-trifluoro-1H-indol-3-yl)ethyl]imidodicarbonimide diamide, trifluoroacetic acid salt as a tan solid. $^1$H NMR (600 MHz, DMSO-d$_6$) ppm 2.93 (s, br, 2H), 3.34-3.41 (m, 2H), 6.36-7.10 (m, 6H), 7.15-7.34 (m, 2H), 11.32 (s, br, 1H); LCMS ESI calculated for C$_{12}$H$_{13}$F$_3$N$_6$: m/z=298; found: m/z=299 (M+H).

Example 51: 1-[2-(6-chloro-7-fluoro-1H-indol-3-yl)ethyl]imidodicarbonimide diamide, trifluoroacetic acid salt

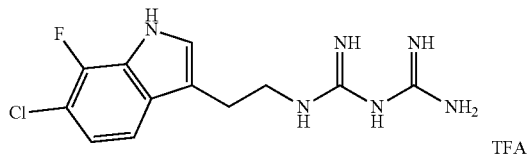 [SMILES: N=C(N)NC(=N)NCCc1c[nH]c2c(F)c(Cl)ccc12]

Commercially available 2-(6-chloro-7-fluoro-1H-indol-3-yl)ethan-1-amine HCl (249 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 48 mg of 1-[2-(6-chloro-7-fluoro-1H-indol-3-yl)ethyl]imidodicarbonimide diamide, trifluoroacetic acid salt as a gummy solid. $^1$H NMR (600 MHz, DMSO-d$_6$) ppm 2.88 (s, br, 2H), 3.32-3.45 (m, 2H), 6.84 (s, br, 6H), 7.03-7.14 (m, 1H), 7.31 (s, 1H), 7.39 (d, J=8.8 Hz, 1H), 11.62 (s, br, 1H); LCMS ESI calculated for $C_{12}H_{14}ClFN_6$: m/z=296; found: m/z=297 (M+H).

Example 52: 1-[2-(6-fluoro-1-methyl-1H-indol-3-yl)ethyl]imidodicarbonimide diamide, trifluoroacetic acid salt

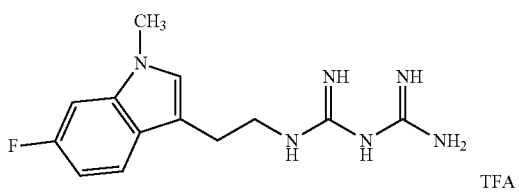 [SMILES: Cn1cc(CCNC(=N)NC(=N)N)c2ccc(F)cc21]

Commercially available 2-(6-fluoro-1-methyl-1H-indol-3-yl)ethan-1-amine HCl (457 mg, 2 mmol) and dicyandiamide (168 mg, 2 mmol) were combined in a dry pear shaped flask under nitrogen. The contents were heated to 170° C. under stirring, with the materials forming a melt once the bath temperature was between 165-170° C. The resulting melt was heated for 3 hr and then allowed to cool to room temperature. The contents were treated with hot MeOH-IPA mixture (30 mL, 1:2) and then filtered. The filtrate was concentrated and the residue was dissolved in 1:1 MeOH—$H_2O$ (2-3 mL) and half of the material was purified by reverse phase semi-preparative HPLC eluting with gradient of $H_2O$-MeOH (Mobile Phase A: $H_2O$ (0.05% TFA); Mobile Phase B: MeOH (0.05% TFA)) for 30 minutes. Mobile Phase B is 0% at the start and reaches 100% at 20 minutes and is maintained there until t=30 minutes to afford 45 mg of 1-[2-(6-fluoro-1-methyl-1H-indol-3-yl)ethyl]imidodicarbonimide diamide, trifluoroacetic acid salt as a gummy solid. $^1$H NMR (600 MHz, DMSO-$d_6$) δ ppm 2.83 (s, br, 2H), 3.34 (d, J=6.2 Hz, 2H), 3.66 (s, 3H), 6.84 (s, br, 7H), 7.12 (s, br, 1H), 7.22 (d, J=10.8 Hz, 1H), 7.51 (dd, J=8.3, 5.4 Hz, 1H); LCMS ESI calculated for $C_{13}H_{17}FN_6$: m/z=276; found: m/z=277 (M+H).

Example 53: 3-(2-(5-chloro-1H-indol-3-yl)ethyl)-1,1-dimethyl imidodicarbonimide diamide trifluoroacetic acid salt

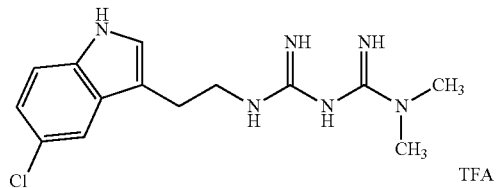 [SMILES: CN(C)C(=N)NC(=N)NCCc1c[nH]c2ccc(Cl)cc12]

Commercially available 2-(5-chloro-1H-indol-3-yl)ethan-1-amine HCl (462 mg, 2 mmol) and N,N-dimethyl dicyandiamide (see Example 23 for preparation) (244 mg, 2.4 mmol) were combined in a dry pear shaped flask under nitrogen. The contents were heated to 170° C. under stirring, with the materials forming a melt once the bath temperature was between 165-170° C. The resulting melt was heated for 3 hr then allowed to cool to room temperature. The contents were treated with hot MeOH-IPA mixture (30 mL, 1:2) and then filtered. Half of the material was purified by reverse phase semi-preparative HPLC eluting with gradient of $H_2O$-MeOH (Mobile Phase A: $H_2O$ (0.05% TFA); Mobile Phase B: MeOH (0.05% TFA)) for 30 minutes. Mobile Phase B is 0% at the start and reaches 100% at 20 minutes and is maintained there until t=30 minutes to afford 3-(2-(5-chloro-1H-indol-3-yl)ethyl)-1,1-dimethyl imidodicarbonimide diamide trifluoroacetic acid salt (40 mg) as a tan solid. $^1$H NMR (600 MHz, DMSO-$d_6$) δ ppm 2.82-2.88 (m, 2H), 2.92 (s, 6H), 3.29-3.35 (m, 2H), 6.33-7.01 (m, 3H), 7.02-7.08 (m, 1H), 7.10-7.23 (m, 1H), 7.24 (d, J=2.5 Hz, 1H), 7.31-7.38 (m, 1H), 7.56 (d, J=2.0 Hz, 1H), 11.05 (s, br, 1H); LCMS ESI calculated for $C_{14}H_{19}ClN_6$: m/z=306; found: m/z=307 (M+H).

Example 54: 3-(2-(6-fluoro-1H-pyrrolo[2,3-b]pyridin-3-yl)ethyl)-1,1-dimethyl imidodicarbonimide diamide trifluoroacetic acid salt

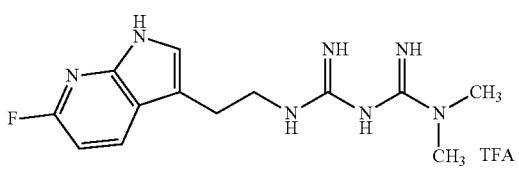 [SMILES: CN(C)C(=N)NC(=N)NCCc1c[nH]c2nc(F)ccc12]

Commercially available 2-(6-fluoro-1H-pyrrolo[2,3-b]pyridin-3-yl)ethan-1-amine HCl (430 mg, 2 mmol) and N,N-dimethyl dicyandiamide (see Example 23 for preparation) (244 mg, 2.4 mmol) were combined in a dry pear shaped flask under nitrogen. The contents were heated to 170° C. under stirring, with the materials forming a melt once the bath temperature was between 165-170° C. The resulting melt was heated for 3 hr then allowed to cool to room temperature. The contents were treated with hot MeOH-IPA mixture (30 mL, 1:2) and then filtered. Half of the material was purified by reverse phase semi-preparative HPLC eluting with gradient of $H_2O$-MeOH (Mobile Phase A: $H_2O$ (0.05% TFA); Mobile Phase B: MeOH (0.05% TFA)) for 30 minutes. Mobile Phase B is 0% at the start and reaches 100% at 20 minutes and is maintained there until t=30 minutes to afford 3-(2-(6-fluoro-1H-pyrrolo[2,3-b]pyridin-3-yl)ethyl)-1,1-dimethyl imidodicarbonimide diamide trifluoroacetic acid salt (45 mg) as a gummy solid. $^1$H NMR (600 MHz, DMSO-$d_6$) δ ppm 2.86 (t, J=7.1 Hz, 2H), 2.89 (s, 6H), 3.34-3.40 (m, 2H), 6.47 (s, br, 1H), 6.70-6.83 (m, 1H), 6.95 (s, br, 1H), 7.24 (d, J=2.0 Hz, 3H), 8.08 (t, J=8.3 Hz, 1H), 11.53 (s, br, 1H); LCMS ESI calculated for $C_{13}H_{18}FN_7$: m/z=291; found: m/z=292 (M+H).

Example 55: 1-[(1H-indol-3-yl)methyl]imidodicarbonimide diamide, trifluoroacetic acid salt

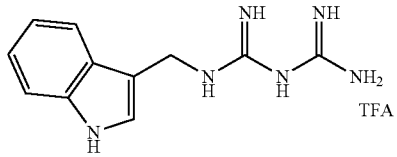 [SMILES: N=C(N)NC(=N)NCc1c[nH]c2ccccc12]

Commercially available (1H-indol-3-yl)methanamine HCl (183 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. Half of the filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 60 mg of 1-[((1H-indol-3-yl)methyl] imidodicarbonimide diamide, trifluoroacetic acid salt as a gummy solid. $^1$H NMR (600 MHz, DMSO-d$_6$) □ ppm 4.43 (d, J=4.7 Hz, 2H), 6.55-7.04 (m, 7H), 7.07 (t, 1H), 7.29-7.33 (m, 1H), 7.33-7.39 (m, 1H), 7.56 (s, br, 1H), 11.00 (s, br, 1H); LCMS ESI calculated for C$_{11}$H$_{14}$N$_6$: m/z=230; found: m/z=231 (M+H).

Example 56: 1-[2-(6-methyl-1H-indol-3-yl)ethyl] imidodicarbonimide diamide, trifluoroacetate salt

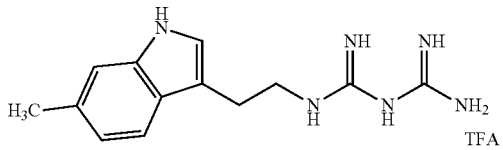 [SMILES: Cc1ccc2c(CCNC(=N)NC(=N)N)c[nH]c2c1]

Commercially available 2-(6-methyl-1H-indol-3-yl) ethan-1-amine HCl (210 mg, 1 mmol) and commercially available 1-carbamimidoyl-2-methyl-isothiourea hydroiodide (264 mg, 2 mmol) were combined in a flask under nitrogen. EtOH (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 132 mg of 1-[2-(6-methyl-1H-indol-3-yl)ethyl]imidodicarbonimide diamide, trifluoroacetate salt as a tan crystals. $^1$H NMR (600 MHz, DMSO-d$_6$) δ ppm 2.37 (s, 3H), 2.82-2.89 (m, 2H), 3.34-3.38 (m, 2H), 6.29-6.80 (s, br, 4H), 6.82 (d, J=7.9 Hz, 1H), 7.07 (s, 1H), 7.13 (s, 1H), 7.83-8.54 (s, br, 3H), 7.41 (d, J=7.9 Hz, 1H), 10.69 (s, 1H); LCMS ESI calculated for C$_{13}$H$_{18}$N$_6$: m/z=258; found: m/z=259 (M+H).

Example 57: 1-[2-(5-trifluoromethoxy-1H-indol-3-yl)ethyl]imidodicarbonimide diamide, trifluoroacetic acid salt

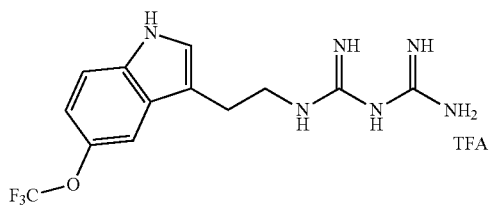 [SMILES: N=C(N)NC(=N)NCCc1c[nH]c2ccc(OC(F)(F)F)cc12]

Commercially available 2-(5-trifluoromethoxy-1H-indol-3-yl)ethan-1-amine HCl (561 mg, 2 mmol) and dicyandiamide (168 mg, 2 mmol) were combined in a dry pear shaped flask under nitrogen. The contents were heated to 180° C. under stirring, with the materials forming a melt once the bath temperature was between 165-170° C.

The resulting melt was heated for 3 hr and then allowed to cool to room temperature. The contents were treated with hot MeOH-IPA mixture (30 mL, 1:2) and then filtered. The filtrate was concentrated and the residue was dissolved in 1:1 MeOH—H$_2$O (2-3 mL) and was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 12 mg of 1-[2-(5-trifluoromethoxy-1H-indol-3-yl)ethyl]imidodicarbonimide diamide, trifluoroacetic acid salt as a colorless oil. $^1$H NMR (600 MHz, DMSO-d$_6$) δ ppm 2.89 (m, 2H), 3.35-3.50 (m; 2H), 6.30-7.02 (s, br, 4H), 7.04 (d, 1H), 7.07-8.14 (s, br, 3H), 7.33 (s., 1H), 7.43 (d., 1H), 7.52 (s, br, 1H), 11.13 (s, br, 1H). LCMS ESI calculated for C$_{13}$H$_{15}$F$_3$N$_6$O: m/z=328; found: m/z=329 (M+H).

Example 58: 1-[2-(5-chloro-6-fluoro-1H-indol-3-yl) ethyl]imidodicarbonimide diamide, trifluoroacetic acid salt

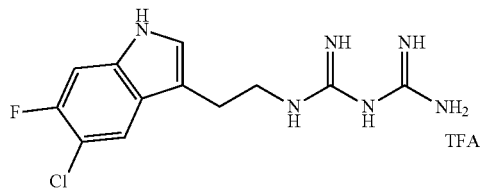 [SMILES: N=C(N)NC(=N)NCCc1c[nH]c2cc(F)c(Cl)cc12]

Commercially available 2-(5-chloro-6-fluoro-1H-indol-3-yl)ethan-1-amine HCl (249 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 51 mg of 1-[2-(5-chloro-6-fluoro-1H-indol-3-yl)ethyl]imidodicarbonimide diamide, trifluoroacetic acid salt as a colorless oil. $^1$H NMR (600 MHz, DMSO-d$_6$) δ ppm 2.83-2.92 (m, 2H), 3.34-3.37 (m, 2H), 6.34-7.25 (s, br, 5H), 7.26 (s, br, 1H), 7.28-7.85 (s, br, 2H), 7.35 (d, J=10.0 Hz, 1H), 7.72 (d, J=7.3 Hz, 1H), 11.14 (s, 1H); LCMS ESI calculated for C$_{12}$H$_{14}$ClFN$_6$: m/z=296; found: m/z=297 (M+H).

Example 59: 1-[2-(7-methyl-1H-indol-3-yl)ethyl] imidodicarbonimide diamide, trifluoroacetic acid salt

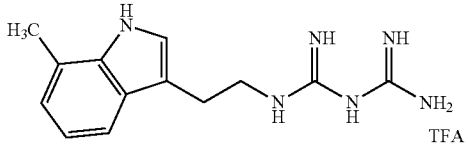 [SMILES: Cc1cccc2c(CCNC(=N)NC(=N)N)c[nH]c12]

Commercially available 2-(7-methyl-1H-indol-3-yl)ethan-1-amine HCl (210 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 30 mg of 1-[2-(7-methyl-1H-indol-3-yl)ethyl]imidodicarbonimide diamide, trifluoroacetic acid salt as a colorless oil. $^1$H NMR (600 MHz, DMSO-d$_6$) δ ppm 2.44 (s, 3H), 2.89 (s, br, 2H), 3.36-3.47 (m, 2H), 6.51-6.85 (s, br, 2H), 6.86-6.92 (m, 2H), 7.17 (s, br, 1H), 6.85-7.97 (s, br, 5H), 7.37 (d, J=7.9 Hz, 1H), 10.83 (s, 1H); LCMS ESI calculated for C$_{13}$H$_{18}$N$_6$: m/z=258; found: m/z=259 (M+H).

Example 60: 1-[2-(4-methyl-1H-indol-3-yl)ethyl] imidodicarbonimide diamide, trifluoroacetic acid salt

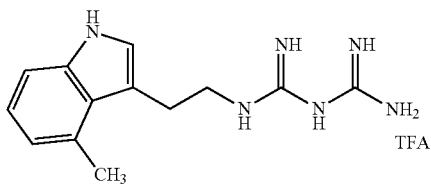

Commercially available 2-(4-methyl-1H-indol-3-yl)ethan-1-amine HCl (210 mg, 1 mmol) and commercially available 1-carbamimidoyl-2-methyl-isothiourea hydroiodide (264 mg, 2 mmol) were combined in a flask under nitrogen. EtOH (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 39 mg of 1-[2-(4-methyl-1H-indol-3-yl)ethyl]imidodicarbonimide diamide, trifluoroacetic acid salt as a colorless oil. $^1$H NMR (600 MHz, DMSO-d$_6$) δ ppm 2.62 (s, 3H), 3.01-3.13 (m, 2H), 3.36-3.41 (m, 2H), 6.24-7.11 (s, br, 4H), 6.70 (d, J=7.0 Hz, 1H), 6.92 (t, 1H), 7.11 (s, br, 1H), 7.16 (d, J=8.2 Hz, 1H), 7.22-8.51 (s, br, 3H), 10.85 (s, br, 1H); LCMS ESI calculated for C$_{13}$H$_{18}$N$_6$: m/z=258; found: m/z=259 (M+H).

Example 61: 1-[2-(4,6-difluoro-1H-indol-3-yl)ethyl] imidodicarbonimide diamide, trifluoroacetic acid salt

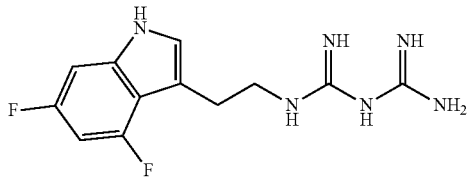 [SMILES: N=C(N)NC(=N)NCCc1c[nH]c2cc(F)cc(F)c12]

Commercially available 2-(4,6-difluoro-1H-indol-3-yl)ethan-1-amine HCl (232 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 22 mg of 1-[2-(4,6-difluoro-1H-indol-3-yl)ethyl]imidodicarbonimide diamide, trifluoroacetic acid salt as a colorless oil. $^1$H NMR (600 MHz, DMSO-d$_6$) δ ppm 2.88-2.98 (m, 2H), 3.34-3.42 (m, 2H), 6.71-6.78 (m, 1H), 6.90 (s, br, 5H), 7.01 (dd, J=9.8, 2.0 Hz, 1H), 7.19 (s, br, 1H), 6.99-7.55 (s, br, 2H), 11.26 (s, br, 1H); LCMS ESI calculated for C$_{12}$H$_{14}$F$_2$N$_6$: m/z=280; found: m/z=281 (M+H).

Example 62: 1-[2-(6-fluoro-1H-indol-3-yl)propyl] imidodicarbonimide diamide, trifluoroacetic acid salt

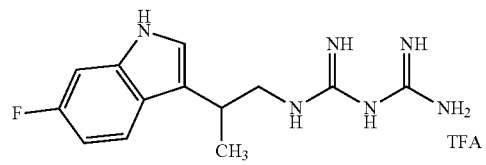

Commercially available 2-(6-fluoro-1H-indol-3-yl)propan-1-amine HCl (229 mg, 1 mmol) and commercially available 1-carbamimidoyl-2-methyl-isothiourea hydroiodide (264 mg, 2 mmol) were combined in a flask under nitrogen. THF (10 mL) and Et$_3$N (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of H$_2$O-MeOH (Mobile Phase A: H$_2$O (0.05% TFA); Mobile Phase B: MeOH (0.05% TFA)) for 30 minutes. Mobile Phase B is 0% at the start and reaches 100% at 20 minutes and is maintained there until t=30 minutes to afford 34 mg of 1-[2-(6-fluoro-1H-indol-3-yl)propyl]imidodicarbonimide diamide, trifluoroacetic acid salt as a colorless oil. $^1$H NMR (600 MHz, DMSO-$d_6$) δ ppm 1.28 (d, 3H), 3.17-3.23 (m, 1H), 3.97-4.07 (m, 2H), 6.45-6.80 (s, br, 5H), 6.80-6.86 (m, 1H), 6.93-7.16 (m, 2H), 7.06-7.17 (m, 2H), 7.54-7.62 (m, 1H), 10.96 (s, br, 1H); LCMS ESI calculated for $C_{13}H_{17}FN_6$: m/z=276; found: m/z=277 (M+H).

Example 63: 1-[2-(6-fluoro-1H-indol-3-yl)-2-methylpropyl]imidodicarbonimide diamide, trifluoroacetic acid salt

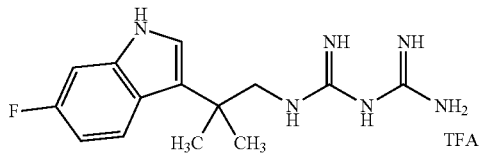 [SMILES: CC(C)(CNC(=N)NC(=N)N)c1c[nH]c2cc(F)ccc12]

Commercially available 2-(6-fluoro-1H-indol-3-yl)-2-methylpropan-1-amine HCl (229 mg, 1 mmol) and commercially available 1-carbamimidoyl-2-methyl-isothiourea hydroiodide (264 mg, 2 mmol) were combined in a flask under nitrogen. THF (10 mL) and $Et_3N$ (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of $H_2O$-MeOH (Mobile Phase A: $H_2O$ (0.05% TFA); Mobile Phase B: MeOH (0.05% TFA)) for 30 minutes. Mobile Phase B is 0% at the start and reaches 100% at 20 minutes and is maintained there until t=30 minutes to afford 12 mg of 1-[2-(6-fluoro-1H-indol-3-yl)-2-methylpropyl]imidodicarbonimide diamide, trifluoroacetic acid salt as a colorless oil. $^1$H NMR (600 MHz, DMSO-$d_6$) δ ppm 1.35 (s, br, 6H), 3.48 (d, J=6.2 Hz, 2H), 6.26-7.10 (s, br, 5H), 6.83 (d, 1H), 7.13 (d, J=2.1 Hz, 1H), 7.20-7.94 (s, br, 2H), 7.69 (dd, 1H), 11.00 (s, br, 1H); LCMS ESI calculated for $C_{14}H_{19}FN_6$: m/z=290; found: m/z=291 (M+H).

Example 64: 1-[2-(5-chloro-7-fluoro-1H-indol-3-yl)ethyl]imidodicarbonimide diamide, trifluoroacetic acid salt

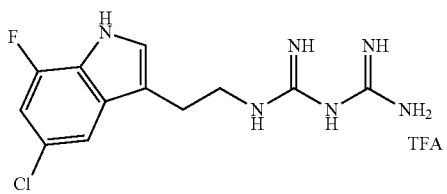 [SMILES: N=C(N)NC(=N)NCCc1c[nH]c2c(F)cc(Cl)cc12]

Commercially available 2-(5-chloro-7-fluoro-1H-indol-3-yl)ethan-1-amine HCl (249 mg, 1 mmol) and commercially available 1-carbamimidoyl-2-methyl-isothiourea hydroiodide (264 mg, 2 mmol) were combined in a flask under nitrogen. THF (10 mL) and $Et_3N$ (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of $H_2O$-MeOH (Mobile Phase A: $H_2O$ (0.05% TFA); Mobile Phase B: MeOH (0.05% TFA)) for 30 minutes. Mobile Phase B is 0% at the start and reaches 100% at 20 minutes and is maintained there until t=30 minutes to afford 219 mg of 1-[2-(5-chloro-7-fluoro-1H-indol-3-yl)ethyl]imidodicarbonimide diamide, trifluoroacetic acid salt as a light brown oil. $^1$H NMR (600 MHz, DMSO-$d_6$) δ ppm 2.79-2.93 (m, 2H), 3.26-3.35 (m, 2H), 6.82 (s, br, 6H), 7.02-7.10 (d, 1H), 7.10-8.25 (s, br, 1H), 7.34 (s, br, 1H), 7.48 (s, 1H); 11.62 (s, br, 1H); LCMS ESI calculated for $C_{12}H_{14}ClFN_6$: m/z=296; found: m/z=297 (M+H).

Example 65: 1-methyl-1-[2-(6-fluoro-1H-indol-3-yl)ethyl]imidodicarbonimide diamide, trifluoroacetic acid salt

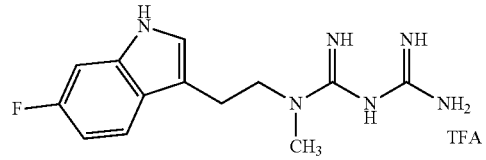 [SMILES: CN(CCc1c[nH]c2cc(F)ccc12)C(=N)NC(=N)N]

Commercially available 2-(6-fluoro-1H-indol-3-yl)-N-methylethan-1-amine HCl (229 mg, 1 mmol) and commercially available 1-carbamimidoyl-2-methyl-isothiourea hydroiodide (264 mg, 2 mmol) were combined in a flask under nitrogen. THF (10 mL) and $Et_3N$ (0.5 mL) were added and the resulting solution was heated to 55-60° C. for 5-6 hours. After cooling to room temperature, the solvent was removed and MeOH (3 mL) was added to the residue followed by filtration. The filtrate was purified by reverse phase semi-preparative HPLC eluting with gradient of $H_2O$-MeOH (Mobile Phase A: $H_2O$ (0.05% TFA); Mobile Phase B: MeOH (0.05% TFA)) for 30 minutes. Mobile Phase B is 0% at the start and reaches 100% at 20 minutes and is maintained there until t=30 minutes to afford 179 mg of 1-methyl-1-[2-(6-fluoro-1H-indol-3-yl)ethyl]imidodicarbonimide diamide, trifluoroacetic acid salt as a pale yellow solid. $^1$H NMR (600 MHz, DMSO-$d_6$) δ ppm 2.87-2.92 (m, 2H), 2.92 (s, br, 3H), 3.54-3.62 (m, 2H), 6.68 (s, br, 4H), 6.81-6.88 (m, 1H), 7.09-7.14 (m, 1H,) 7.17 (s, br, 1H), 7.24 (s, br, 2H), 7.57 (dd, J=8.6, 5.6 Hz, 1H), 10.96 (s, br, 1H); LCMS ESI calculated for $C_{13}H_{17}FN_6$: m/z=276; found: m/z=277 (M+H).

Biological Data

Metformin is well-established in the literature to inhibit mitochondrial complex I and oxygen consumption rate, resulting in activation of AMPK. See, e.g., El-Mir, M. Y., Nogueira, V., Fontaine, E., Averet, N., Rigoulet, M., and Leverve, X. *Dimethylbiguanide inhibits cell respiration via an indirect effect targeted on the respiratory chain complex I*. J. Biol Chem 2000, 275:223; and Stephenne, X., Foretz, M., Taleux, N., van der Zon, G. C., Sokal, E., Hue, L., Viollet, B., and Guigas, B. *Metformin activates AMP-activated protein kinase in primary human hepatocytes by decreasing cellular energy status*. Diabetologia 2011, 54 (12): 3101-3110, each incorporated by reference with regard to such testing. The compounds of the present invention are similarly tested in an oxygen consumption rate (OCR) assay to evaluate the functional activity of test compounds in cells.

In brief, the assay uses HEK293 cells stably transfected with the human OCT1, OCT2, OCT3, PMAT, or MATE1 transporters to determine a compound's relative transporter selectivity and its effect on the rate of oxygen consumption relative to control (Neo) cells. The MitoXpress Xtra oxygen-sensitive fluorophore is used to monitor oxygen consumption rates in the presence and absence of compound treatments. The analogs were tested at eight (8) different concentrations in triplicate to determine a relative $IC_{50}$ value.

A summary description of the protocol is as follows:

HEK293 cells transformed with human organic cation transporters were plated in collagen coated, 96-well black-walled microclear plates (Greiner-Bio 1, #655956) at 60,000 cells per well in growth medium (DMEM (LG), 10% FBS, 400 μg/ml G418). Cells were incubated overnight to allow attachment. The outer columns (1 and 12) are not seeded with cells, as controls. The next day, plating medium was removed and replaced with 150 μL of assay medium (DMEM/F12 (PRF), 5% FBS, antibiotics) containing compound dilutions. A 3-fold serial dilution was prepared in the assay medium and transferred to the empty wells. The outer columns and column 11 received 150 μL of assay medium only. 10 μL of MitoXpress Xtra reagent was added to each test well, and 100 μL of pre-warmed mineral oil was overlayed in each well to create a seal. Dual read time-resolved fluorescence (BMG FluoStar Galaxy reader) was measured over 2 hours with measurements taken every 2 minutes. Excitation is 340 nm, Emission is 650 nm. For lifetime analysis, two measurements per well were taken: 1) delay of 30 μs, with a window of 30 μs; and 2) delay of 70 μs with a window of 30 μs. Background TRF values from A1-D1 were subtracted from all readings. A ratiometric analysis was performed to determine changes in the Lifetime fluorescence signal:Lifetime (μs) $[T]=(D2-D1)/\ln(W1/W2)$, where D is delay; W is fluorescence window value at each time point. Lifetime slopes were calculated using each Lifetime measurement over time. $IC_{50}$ values were determined by plotting lifetime slope values vs. compound concentration.

TABLE 1

Oxygen Consumption Rate (OCR) of Examples 1-65

| Comp. # | Structure | OCT 1 | OCT 2 | OCT 3 | Neo | MATE 1 | PMAT |
|---|---|---|---|---|---|---|---|
| Metformin | 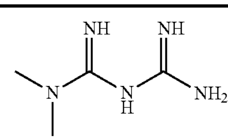 | 409 | 320 | 133 | >3000 | >5000 | 288 |
| Ex 1 | 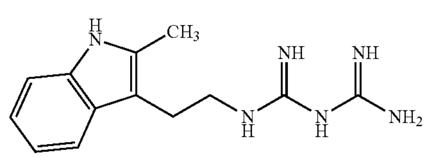 [SMILES: Cc1[nH]c2ccccc2c1CCNC(=N)NC(=N)N] | 1267 | 36 | 37 | >5000 | 30%[1] | 3 |
| Ex 2 | 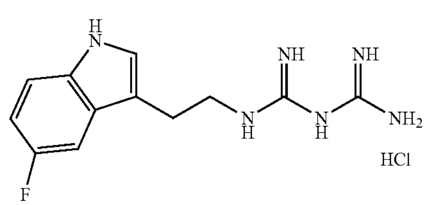 [SMILES: N=C(N)NC(=N)NCCc1c[nH]c2ccc(F)cc12 ; Cl] | >1000 | 7 | 8 | >1000 | >1000 | 5 |
| Ex 3 | 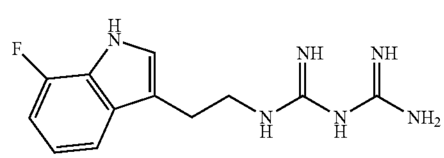 [SMILES: N=C(N)NC(=N)NCCc1c[nH]c2c(F)cccc12] | 4 | 7 | 4 | 677 | 20 | 4 |
| Ex 4 | 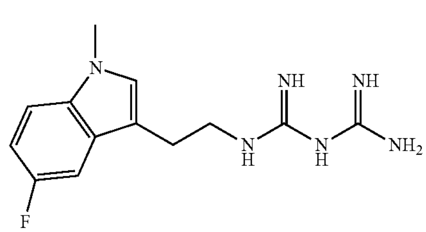 [SMILES: Cn1cc(CCNC(=N)NC(=N)N)c2cc(F)ccc21] | 23 | 10 | 5 | 678 | 1568 | 41%[2] |

TABLE 1-continued

Oxygen Consumption Rate (OCR) of Examples 1-65

| Comp. # | Structure | (IC$_{50}$, μM) | | | | | |
|---|---|---|---|---|---|---|---|
| | | OCT 1 | OCT 2 | OCT 3 | Neo | MATE 1 | PMAT |
| Ex 5 | 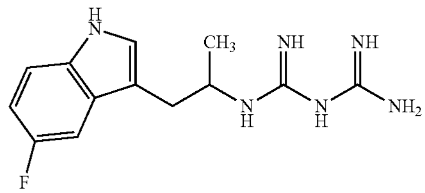 [SMILES: CC(Cc1c[nH]c2ccc(F)cc12)NC(=N)NC(=N)N] | 1069 | 23 | 18 | 1877 | 65% | 12% |
| Ex 6 | 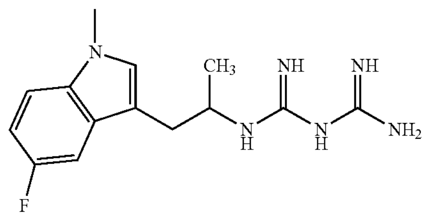 [SMILES: CC(Cc1cn(C)c2ccc(F)cc12)NC(=N)NC(=N)N] | >10000 | 52 | 46 | >10000 | 18% | 8% |
| Ex 7 | 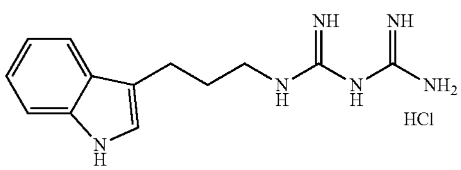 [SMILES: N=C(N)NC(=N)NCCCc1c[nH]c2ccccc12 ; Cl] | 106 | 20 | 8 | >10000 | 36% | 7% |
| Ex 8 | 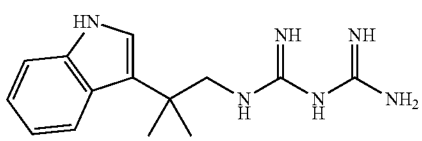 [SMILES: CC(C)(CNC(=N)NC(=N)N)c1c[nH]c2ccccc12] | >1000 | 15 | 29 | >1000 | 31% | 20% |
| Ex 9 | 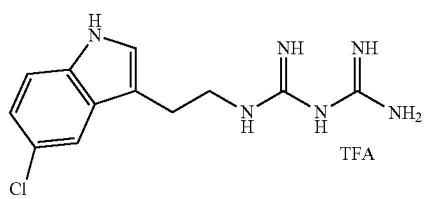 [SMILES: N=C(N)NC(=N)NCCc1c[nH]c2ccc(Cl)cc12] | 12 | 5 | 5 | 70 | 171 | 53% |
| Ex 10 | 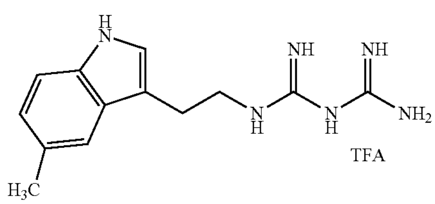 | 36 | 9 | 7 | 439 | 2190 | 43% |
| Ex 11 | 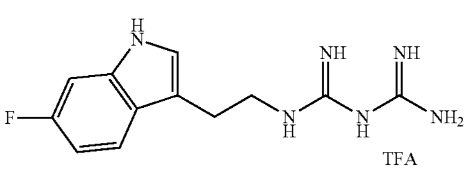 [SMILES: N=C(N)NC(=N)NCCc1c[nH]c2cc(F)ccc12] | 25 | 12 | 6 | 214 | 57 | 3 |

TABLE 1-continued

Oxygen Consumption Rate (OCR) of Examples 1-65

| Comp. # | Structure | OCT 1 | OCT 2 | OCT 3 | Neo | MATE 1 | PMAT |
|---|---|---|---|---|---|---|---|
| Ex 12 | 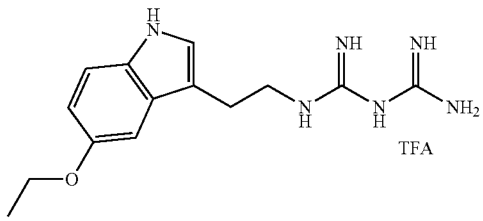 [SMILES: CCOc1ccc2[nH]cc(CCNC(=N)NC(=N)N)c2c1] | 952 | 14 | 10 | 1152 | −8% | NT |
| Ex 13 | 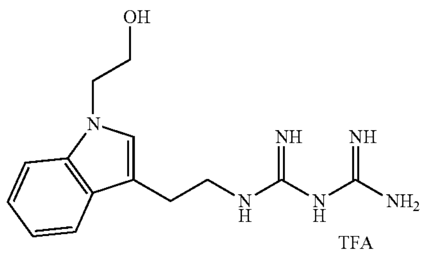 [SMILES: N=C(N)NC(=N)NCCc1cn(CCO)c2ccccc12] | 1594 | 20 | 20 | 2515 | 22% | NT |
| Ex 14 | 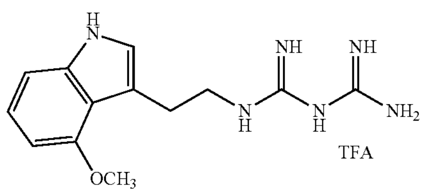 [SMILES: COc1cccc2[nH]cc(CCNC(=N)NC(=N)N)c12] | 9 | 6 | 5 | 1313 | 39% | NT |
| Ex 15 | 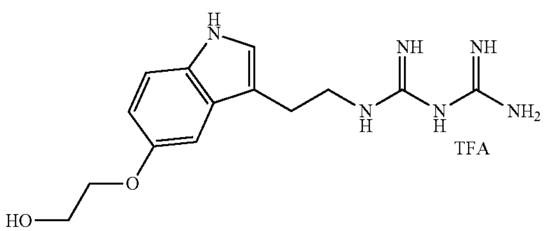 [SMILES: N=C(N)NC(=N)NCCc1c[nH]c2ccc(OCCO)cc12] | 3665 | 19 | 86 | >10000 | −17% | NT |
| Ex 16 | 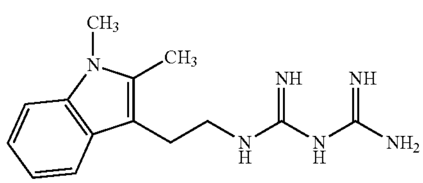 [SMILES: Cc1c(CCNC(=N)NC(=N)N)c2ccccc2n1C] | 275 | 16 | 10 | 1207 | 10% | 36% |
| Ex 17 | 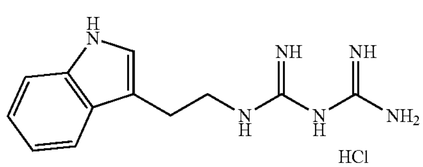 [SMILES: N=C(N)NC(=N)NCCc1c[nH]c2ccccc12 ; Cl] | >5000 | 10 | 8 | >5000 | 4837 | 54% |
| Ex 18 | 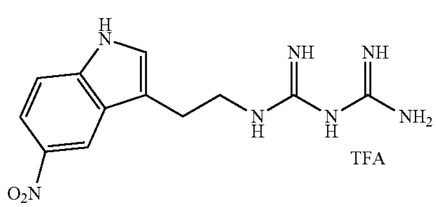 [SMILES: N=C(N)NC(=N)NCCc1c[nH]c2ccc([N+](=O)[O-])cc12] | 12 | 7 | 11 | 1408 | −26% | 27% |

(IC$_{50}$, μM)

TABLE 1-continued

Oxygen Consumption Rate (OCR) of Examples 1-65

| Comp. # | Structure | (IC$_{50}$, µM) | | | | | |
|---|---|---|---|---|---|---|---|
| | | OCT 1 | OCT 2 | OCT 3 | Neo | MATE 1 | PMAT |
| Ex 19 | (structure) TFA | 20 | 22 | >3000 | >3000 | 14% | NT |
| Ex 20 | (structure) HCl | 772 | 20 | 202 | 605 | NT | NT |
| Ex 21 | (structure) AcOH | 23 | 129 | 27 | >3000 | 1537 | 27% |
| Ex 22 | (structure) HCl | 3708 | 177 | >1000 | 3242 | 2980 | −7% |
| Ex 23 | (structure) HCl | >3000 | 32 | 1395 | >3000 | >10000 | 4% |
| Ex 24 | (structure) HCl | >3000 | 20 | 822 | 1590 | >10000 | NT |
| Ex 25 | (structure) TFA | 256 | 4 | 8 | 51 | 44% | NT |
| Ex 26 | (structure) TFA | 4 | 2 | 3 | 90 | NT | 2 |

TABLE 1-continued

Oxygen Consumption Rate (OCR) of Examples 1-65

| Comp. # | Structure | (IC$_{50}$, µM) | | | | | |
|---|---|---|---|---|---|---|---|
| | | OCT 1 | OCT 2 | OCT 3 | Neo | MATE 1 | PMAT |
| Ex 27 | 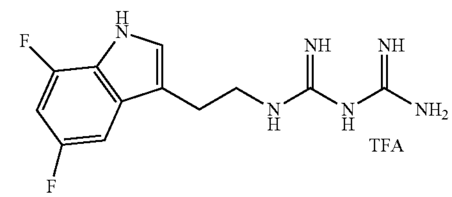 [SMILES: N=C(N)NC(=N)NCCc1c[nH]c2c(F)cc(F)cc12 ; "TFA"] | 15 | 4 | 89 | 291 | NT | NT |
| Ex 28 | 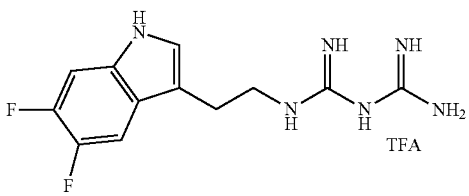 [SMILES: N=C(N)NC(=N)NCCc1c[nH]c2cc(F)c(F)cc12 ; "TFA"] | 3 | 3 | 5 | 604 | NT | NT |
| Ex 29 | 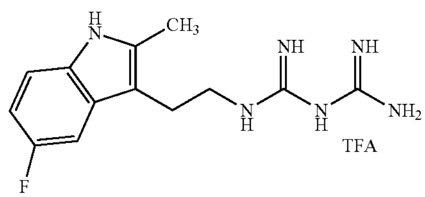 [SMILES: Cc1[nH]c2ccc(F)cc2c1CCNC(=N)NC(=N)N ; "TFA"] | 19 | 8 | >1000 | >100 | NT | NT |
| Ex 30 | 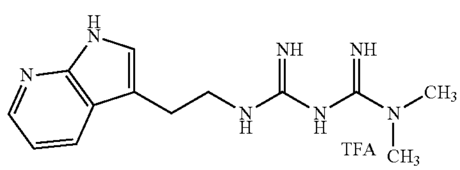 [SMILES: CN(C)C(=N)NC(=N)NCCc1c[nH]c2ncccc12 ; "TFA"] | 1315 | 101 | 2327 | 864 | NT | NT |
| Ex 31 | 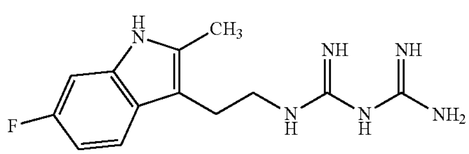 [SMILES: Cc1[nH]c2cc(F)ccc2c1CCNC(=N)NC(=N)N] | 38 | 10 | 3648 | 4874 | 13352 | 35% |
| Ex 32 | 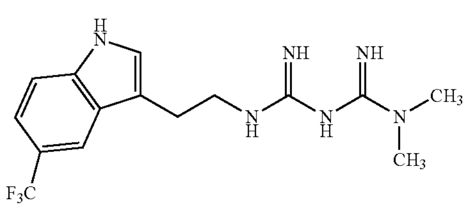 [SMILES: CN(C)C(=N)NC(=N)NCCc1c[nH]c2ccc(C(F)(F)F)cc12] | 381 | 18 | 432 | 397 | 681 | 10% |
| Ex 33 | 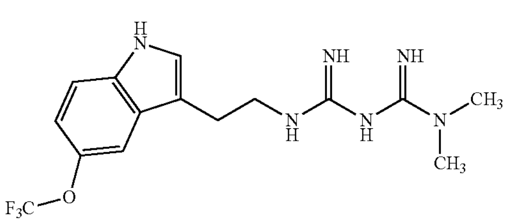 [SMILES: CN(C)C(=N)NC(=N)NCCc1c[nH]c2ccc(OC(F)(F)F)cc12] | 196 | 9 | 204 | 156 | 218 | NT |

TABLE 1-continued

Oxygen Consumption Rate (OCR) of Examples 1-65

| Comp. # | Structure | (IC$_{50}$, μM) | | | | | |
|---|---|---|---|---|---|---|---|
| | | OCT 1 | OCT 2 | OCT 3 | Neo | MATE 1 | PMAT |
| Ex 34 | 4-Cl-tryptamine biguanide | 3 | 2 | 29 | 184 | 19 | 2 |
| Ex 35 | 6-Cl-tryptamine biguanide | 7 | 4 | 97 | 205 | 20 | 68% |
| Ex 36 | 7-Cl-tryptamine biguanide | 4 | 4 | 91 | 409 | 26 | 55% |
| Ex 37 | 6-F-5-CH$_3$-tryptamine biguanide | 6 | 3 | 23 | 326 | 70 | NT |
| Ex 38 | 7-Cl-5-F-tryptamine biguanide | 93 | 65 | 117 | 8759 | 2050 | NT |
| Ex 39 | 1-CH$_3$-7-azatryptamine biguanide | 3 | 2 | 149 | 205 | 168 | NT |
| Ex 40 | 5-Cl-7-azatryptamine biguanide | 18 | 14 | 169 | >1000 | 1470 | NT |
| Ex 41 | 5,6,7-triF-tryptamine biguanide | 5 | 6 | 301 | 460 | 675 | 6 |

TABLE 1-continued

Oxygen Consumption Rate (OCR) of Examples 1-65

| Comp. # | Structure | (IC$_{50}$, µM) | | | | | |
|---|---|---|---|---|---|---|---|
| | | OCT 1 | OCT 2 | OCT 3 | Neo | MATE 1 | PMAT |
| Ex 42 | 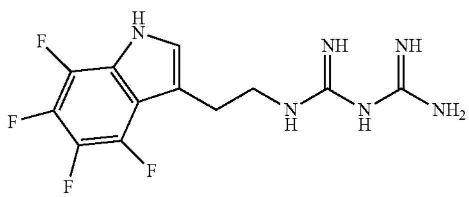 | 7 | 4 | 130 | 129 | 183 | 5 |
| Ex 43 | 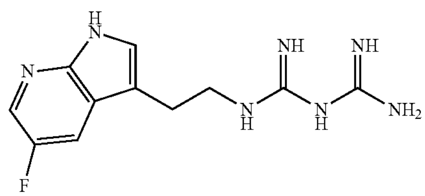 [SMILES: N=C(N)NC(=N)NCCc1c[nH]c2ncc(Cl)cc12] | 26 | 43 | 23 | 11036 | 2225 | 23 |
| Ex 44 | 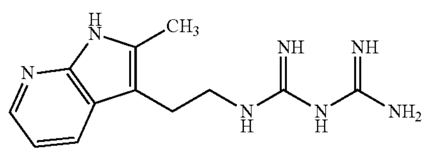 [SMILES: Cc1[nH]c2ncccc2c1CCNC(=N)NC(=N)N] | 290 | 225 | 2252 | 1656 | 474 | NT |
| Ex 45 | 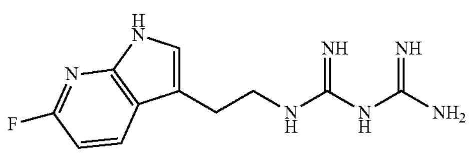 [SMILES: N=C(N)NC(=N)NCCc1c[nH]c2nc(F)ccc12] | 32 | 61 | 20 | 11411 | >3000 | 14 |
| Ex 46 | 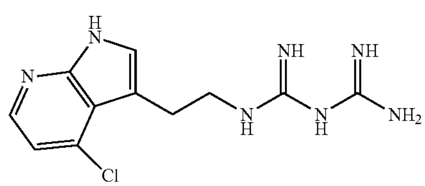 [SMILES: N=C(N)NC(=N)NCCc1c[nH]c2nccc(Cl)c12] | 89 | 510 | 28 | 2639 | 335 | NT |
| Ex 47 | 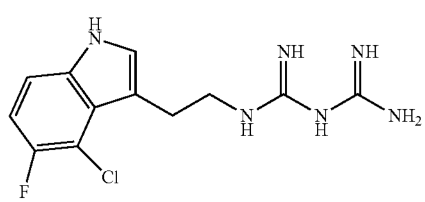 | 4 | 65 | 3 | 101 | 22 | NT |
| Ex 48 | 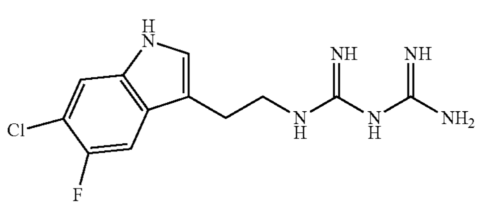 [SMILES: N=C(N)NC(=N)NCCc1c[nH]c2cc(Cl)c(F)cc12] | 10 | 51 | 6 | 210 | 101 | 61% |

TABLE 1-continued

Oxygen Consumption Rate (OCR) of Examples 1-65

| Comp. # | Structure | (IC$_{50}$, µM) | | | | | |
|---|---|---|---|---|---|---|---|
| | | OCT 1 | OCT 2 | OCT 3 | Neo | MATE 1 | PMAT |
| Ex 49 | 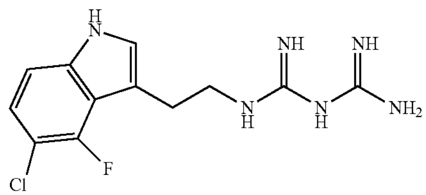 [SMILES: N=C(N)NC(=N)NCCc1c[nH]c2ccc(Cl)c(F)c12] | 3 | 73 | 3 | 155 | 64 | NT |
| Ex 50 | 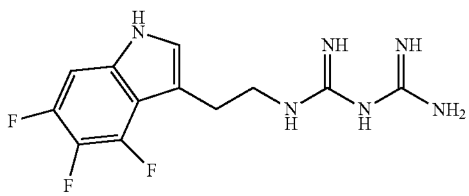 [SMILES: N=C(N)NC(=N)NCCc1c[nH]c2cc(F)c(F)c(F)c12] | 3 | 111 | 2 | 181 | 102 | NT |
| Ex 51 | 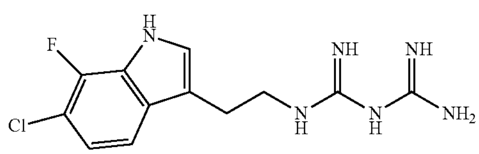 [SMILES: N=C(N)NC(=N)NCCc1c[nH]c2c(F)c(Cl)ccc12] | 13 | 251 | 8 | 542 | 597 | NT |
| Ex 52 | 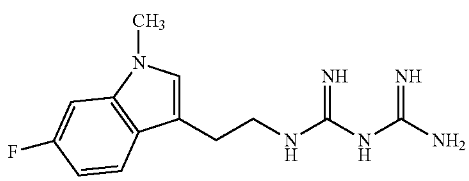 [SMILES: Cn1cc(CCNC(=N)NC(=N)N)c2ccc(F)cc21] | 4 | 3 | 3 | 388 | 32 | NT |
| Ex 53 | 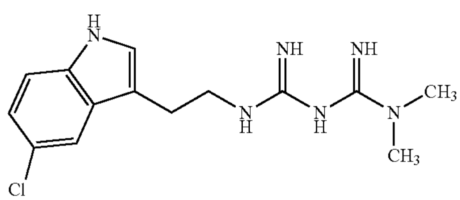 [SMILES: CN(C)C(=N)NC(=N)NCCc1c[nH]c2ccc(Cl)cc12] | 520 | 415 | 498 | 422 | 398 | NT |
| Ex. 54 | 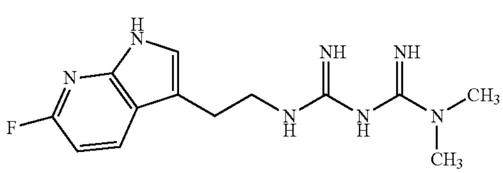 [SMILES: CN(C)C(=N)NC(=N)NCCc1c[nH]c2nc(F)ccc12] | 10739 | >3000 | 5917 | 4597 | 4951 | NT |
| Ex 55 | 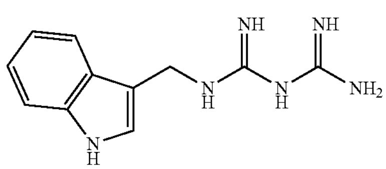 [SMILES: N=C(N)NC(=N)NCc1c[nH]c2ccccc12] | 8 | 9 | 49 | 1395 | 1646 | 10% |
| Ex 56 | 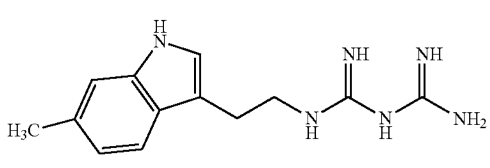 [SMILES: Cc1ccc2c(CCNC(=N)NC(=N)N)c[nH]c2c1] | 8 | 5 | 219 | 895 | 769 | 43% |

TABLE 1-continued

Oxygen Consumption Rate (OCR) of Examples 1-65

| Comp. # | Structure | (IC$_{50}$, μM) | | | | | |
|---|---|---|---|---|---|---|---|
| | | OCT 1 | OCT 2 | OCT 3 | Neo | MATE 1 | PMAT |
| Ex 57 | 5-(trifluoromethoxy)tryptamine biguanide | 18 | 10 | 282 | 255 | 631 | 6% |
| Ex 58 | 5-chloro-6-fluorotryptamine biguanide | 3 | 2 | 86 | 191 | 35 | NT |
| Ex 59 | 7-methyltryptamine biguanide | 9 | 7 | 38 | 1294 | 112 | 47% |
| Ex 60 | 4-methyltryptamine biguanide | 12 | 3 | 427 | 1642 | 636 | NT |
| Ex 61 | 4,6-difluorotryptamine biguanide | 3 | 4 | 58 | 333 | 62 | NT |
| Ex 62 | 6-fluoro-α-methyltryptamine biguanide | 24 | 8 | 86 | 3430 | 3430 | NT |
| Ex 63 | 6-fluoro-β,β-dimethyltryptamine biguanide | 49 | 9 | 988 | 1751 | 3785 | NT |
| Ex 64 | 5-chloro-7-fluorotryptamine biguanide | 5 | 5 | 307 | 282 | 370 | NT |

TABLE 1-continued

Oxygen Consumption Rate (OCR) of Examples 1-65

| | | (IC$_{50}$, μM) | | | | | |
|---|---|---|---|---|---|---|---|
| Comp. # | Structure | OCT 1 | OCT 2 | OCT 3 | Neo | MATE 1 | PMAT |
| Ex 65 | | 40 | 35 | 2634 | 8413 | 354 | NT |

[1] % Inhibition at 1000 μM test concentration;
[2] % Inhibition at 10 μM;
NT = not tested Compounds of formula (I) have also been evaluated in an acute model of type 2 diabetes (glucose disposal). An Oral Glucose Tolerance Test (OGTT) was performed in order to demonstrate oral activity of test compounds. A general description of the protocol is as follows [Charles River Laboratories International, Inc. standard OGTT protocol]:

Male C57Bl/6 mice at ~9 weeks of age were group housed in larger cages at 8/cage. Standard rodent chow (Purina Lab Diet 5001) and drinking water were provided ad libitum prior to study day.

Each cage of 8 animals were assigned to a treatment group, making one cage as a single treatment. Compounds were formulated in 20% PEG400 the morning of the dose.

All treatments were administered to the appropriate animals by oral gavage. The dose volume for each animal (10 mL/kg) was based on the most recent body weight measurement taken at time of fasting. Observations were recorded at each dose and any abnormalities were recorded and reported to the Study Director.

On the day of dosing, a glucose tolerance test was conducted following a 5 hour fast (food removed ~0800 hrs). At time of food removal animals were also weighed and tail marked for identification. At ~1300 hours a baseline blood glucose was checked via handheld glucometer on all mice and all mice were gavaged with their respective compound dose (test agent dose ranged from 10-500 mg/kg). 60 minutes later (~1400 hrs) all mice were gavaged with glucose at 3 g/kg (10 mL/kg) at a rate of 30 seconds per mouse.

Blood glucose was checked via glucometer at the following times relative to glucose dose: −60 minutes (just prior to compound dose), 0 (just prior to glucose dose), 15, 30, 60, 90, and 120 minutes.

Following the 120 minute timepoint, all mice were sacrificed (via CO$_2$ asphyxiation) and a terminal cardiac puncture blood was collected in a serum separator tube and placed at room temperature for 30-40 mins. Samples were spun at 2,200×g for 10 minutes at 22° C. The processed serum was collected into tubes and stored at −70° C.

Figure 2:
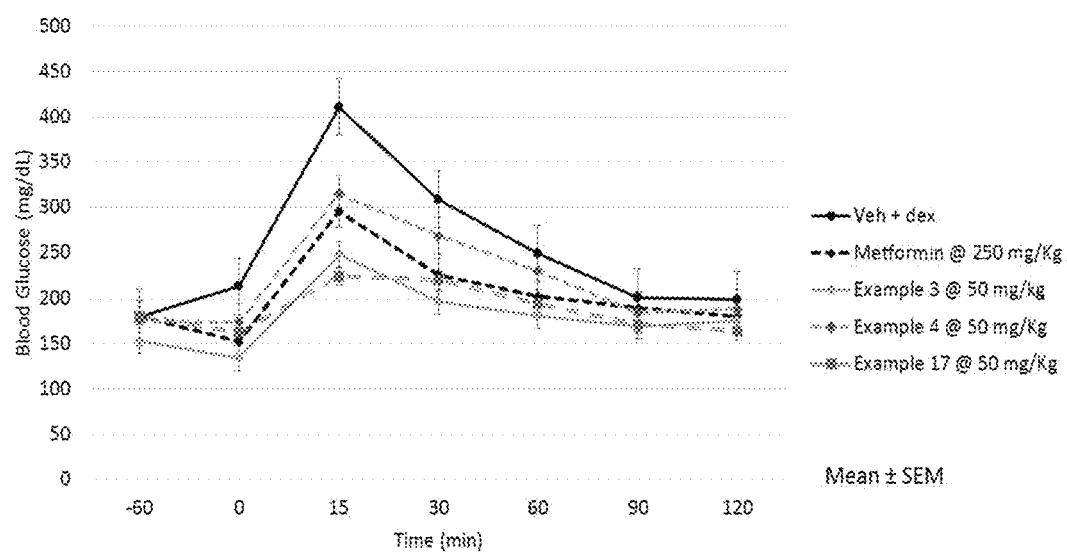
FIG. 2 is an illustration of the improved effect of the compounds of the present invention on blood glucose levels over time at the depicted dose.

As shown in FIGS. 1 and 2, the compounds of the present invention provide statistically significant improvements on blood glucose levels in an OGTT assay.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

That which is claimed is:

1. A compound of formula:

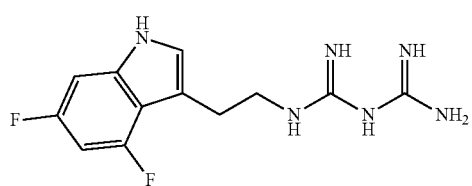 [SMILES: N=C(N)NC(=N)NCCc1c[nH]c2cc(F)cc(F)c12]

or a pharmaceutically acceptable salt thereof.

* * * * *